US007482134B2

(12) United States Patent
Jang et al.

(10) Patent No.: US 7,482,134 B2
(45) Date of Patent: Jan. 27, 2009

(54) SIGNALS AND MOLECULAR SPECIES INVOLVED IN SENESCENCE

(75) Inventors: Ik-Soon Jang, Seoul (KR); Eui-Ju Yeo, Kyonggi-do (KR); Sang-Chul Park, Seoul (KR)

(73) Assignee: Seoul National University Industry Foundation, Shinlim-Dong, Kwanak-Gu, Seoul (KR)

( * ) Notice: Subject to any disclaimer, the term of this patent is extended or adjusted under 35 U.S.C. 154(b) by 95 days.

(21) Appl. No.: 10/517,269

(22) PCT Filed: Jun. 5, 2002

(86) PCT No.: PCT/KR02/01067

§ 371 (c)(1),
(2), (4) Date: Sep. 26, 2005

(87) PCT Pub. No.: WO03/104482

PCT Pub. Date: Dec. 18, 2003

(65) Prior Publication Data

US 2006/0099568 A1    May 11, 2006

(51) Int. Cl.
*C12Q 1/50*    (2006.01)
(52) U.S. Cl. ........................................... 435/17
(58) Field of Classification Search ............. None
See application file for complete search history.

(56) References Cited

U.S. PATENT DOCUMENTS

| 5,705,511 A | 1/1998 | Hudkins et al. |
| 5,712,262 A | 1/1998 | Spiegel |

FOREIGN PATENT DOCUMENTS

| WO | WO 00/60062 A2 | 10/2000 |
| WO | WO 01/23615 A1 | 4/2001 |

OTHER PUBLICATIONS

Chiang et al. The J of Clin. Endo. & Metabolism 2000;85(10):3828-3839.*
Chaves et al. Gerontology 2002;48:354-359.*
Gupta, Sudhir, "Membrane Signal Transduction in T Cells in Aging Humans," Annals of the New York Academy of Sciences 568: 277-282 (1989).

* cited by examiner

*Primary Examiner*—Jon P Weber
*Assistant Examiner*—Bin Shen
(74) *Attorney, Agent, or Firm*—Joseph Hyosuk Kim; JHK Law

(57) ABSTRACT

The present invention relates to (a) a method for detecting a senescent cell, which comprises measuring a relative alteration to young cell in a signal or molecular species involved in signal transduction; (b) a method; and (c) a composition for modulating cellular senescence comprising treating a senescent cell with the effective amount of an inhibitor of adenylyl cyclase or an inhibitor of protein kinase A.

4 Claims, 22 Drawing Sheets

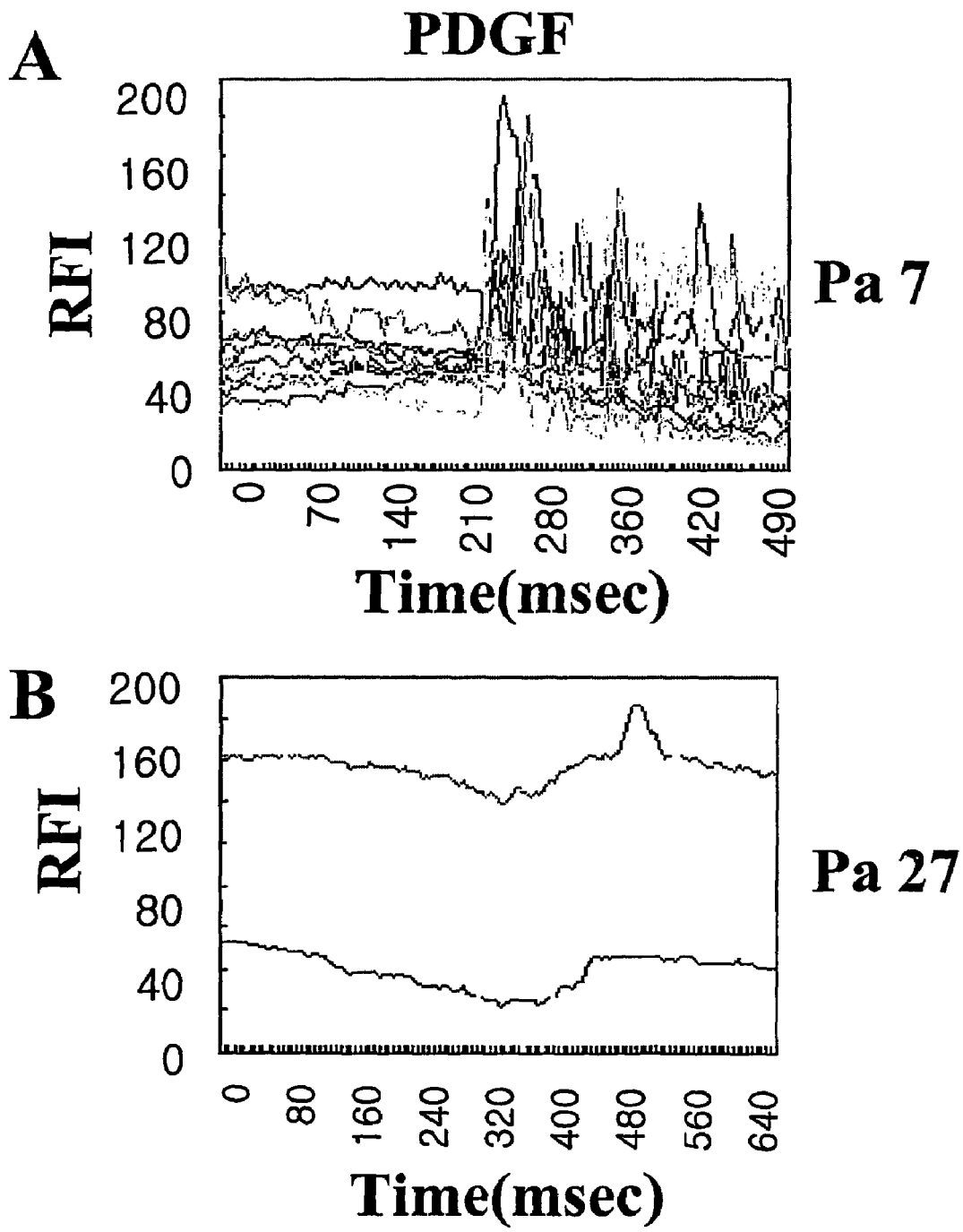

Fig. 1
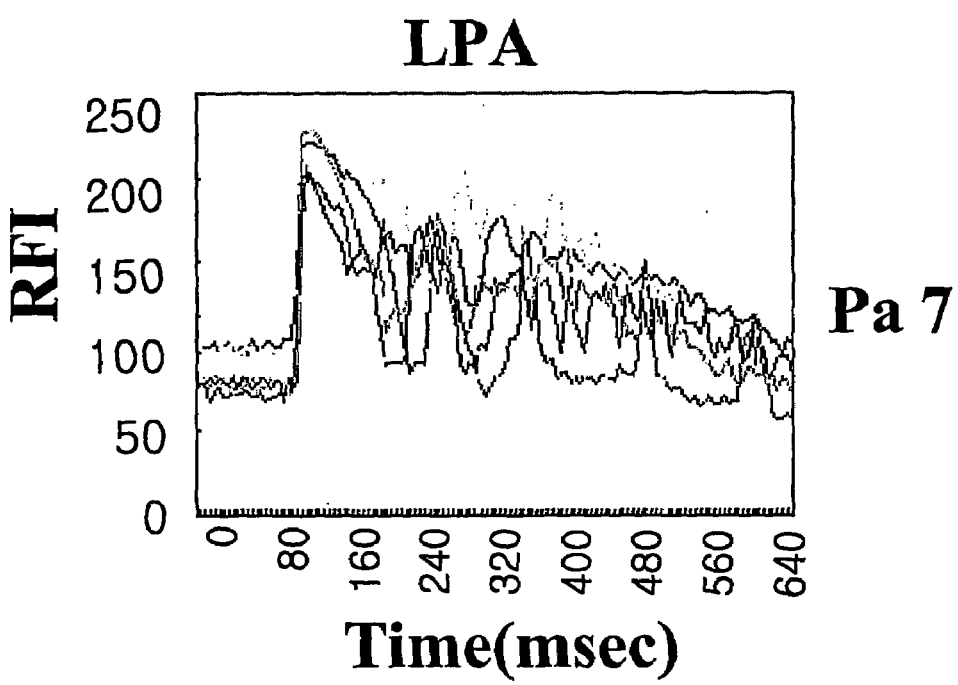
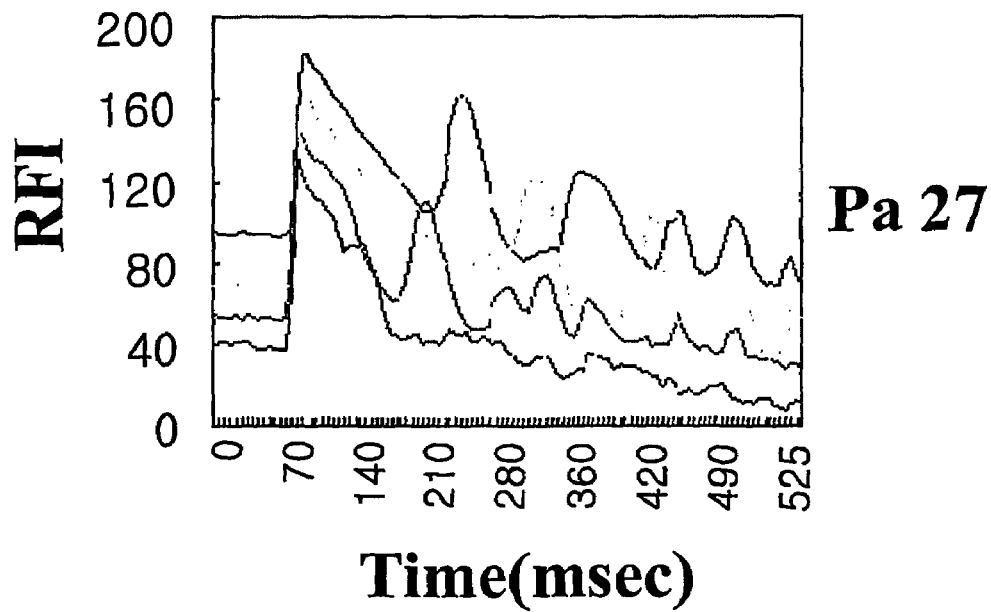

Fig. 5
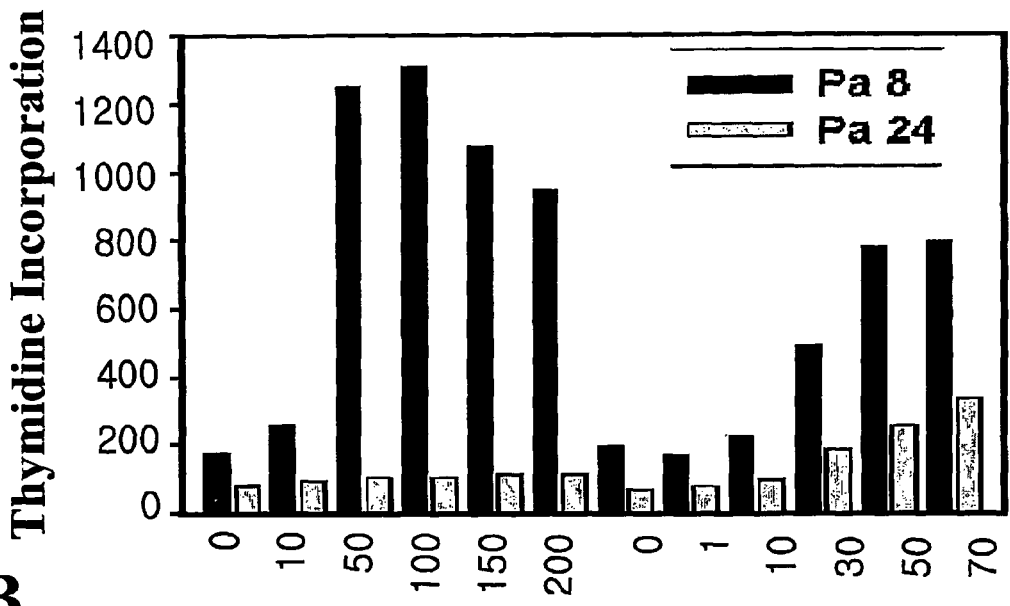
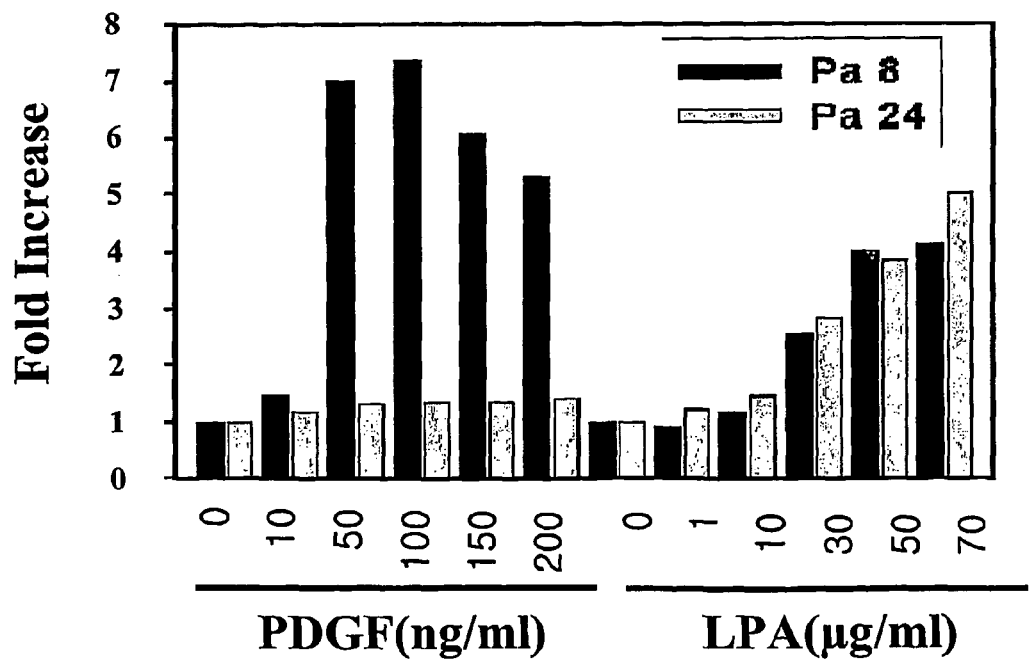
PDGF(ng/ml)     LPA(µg/ml)

Fig. 7
A
Pa 6   Pa 18   Pa 25
 PLC-γ1
 Actin
B
Pa 8  Pa 10  Pa 18  Pa 27
 PDGFR
 Actin Fig. 8
A
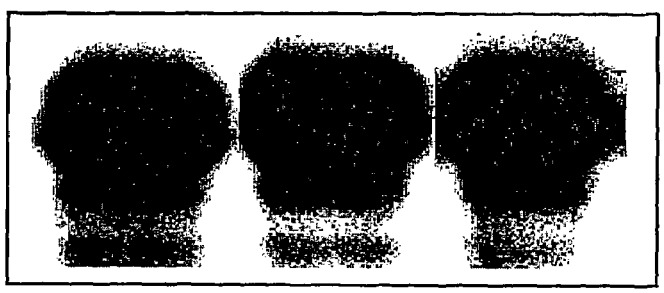 PKCs
 Actin
B
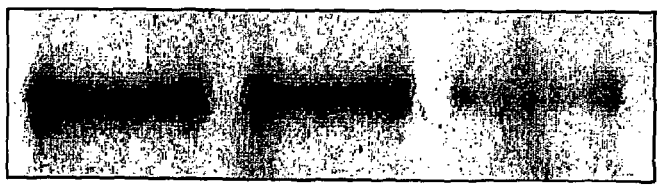 ◄ PLD1
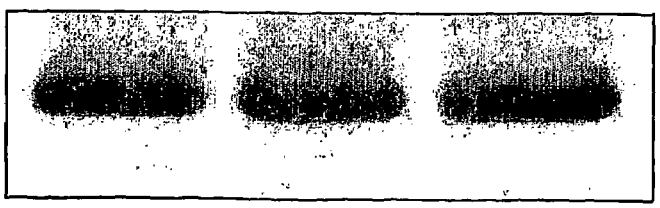 ◄ Unknown (p15)

Fig. 9
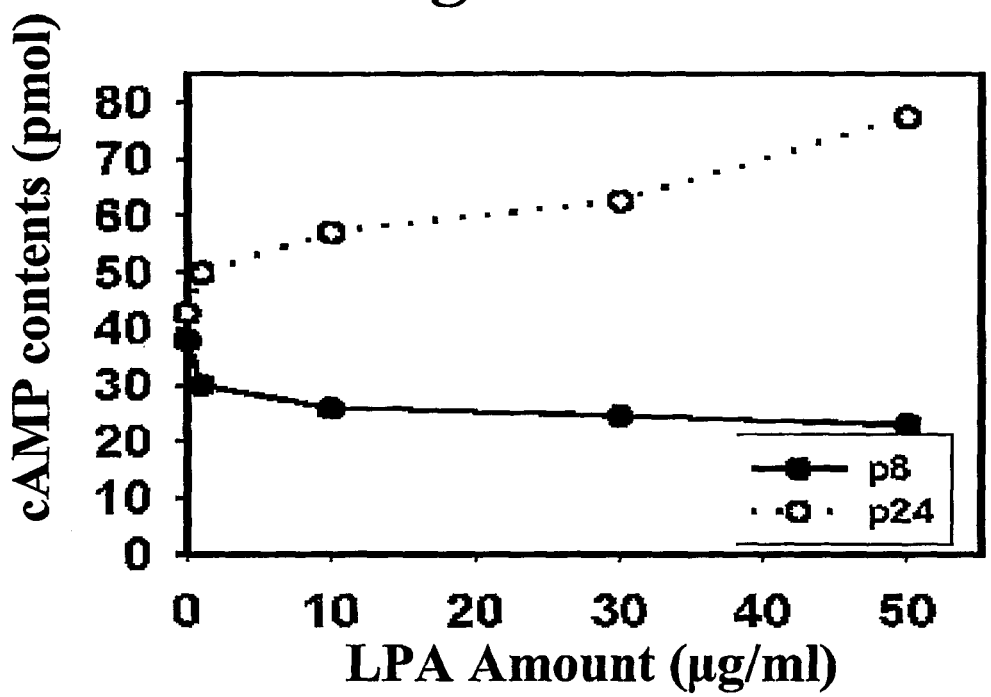
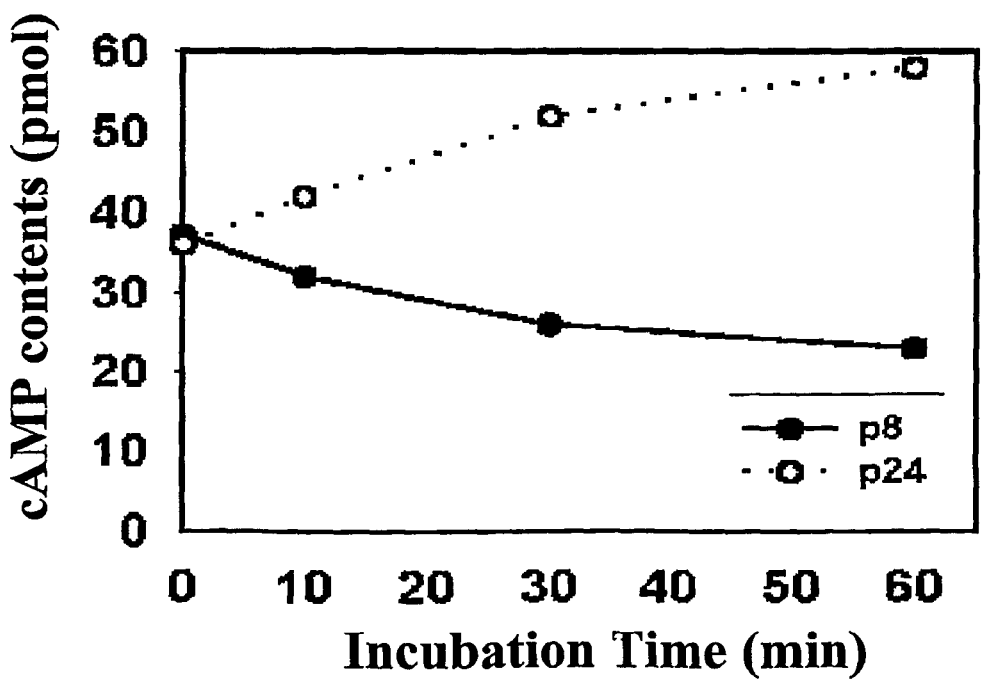

Fig. 10
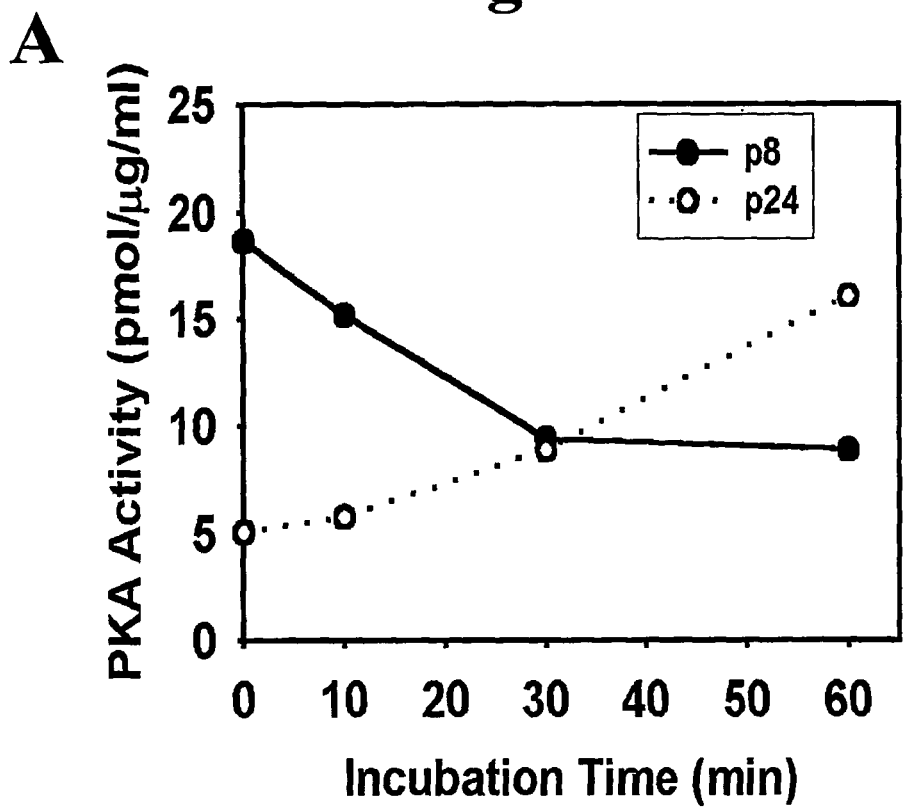
B        Phopho CREB
Pa 8 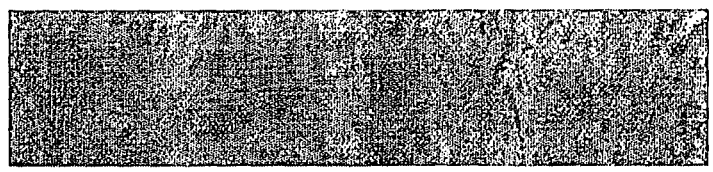
Pa 24 
0        10        30        60  (min)

A Fig. 11
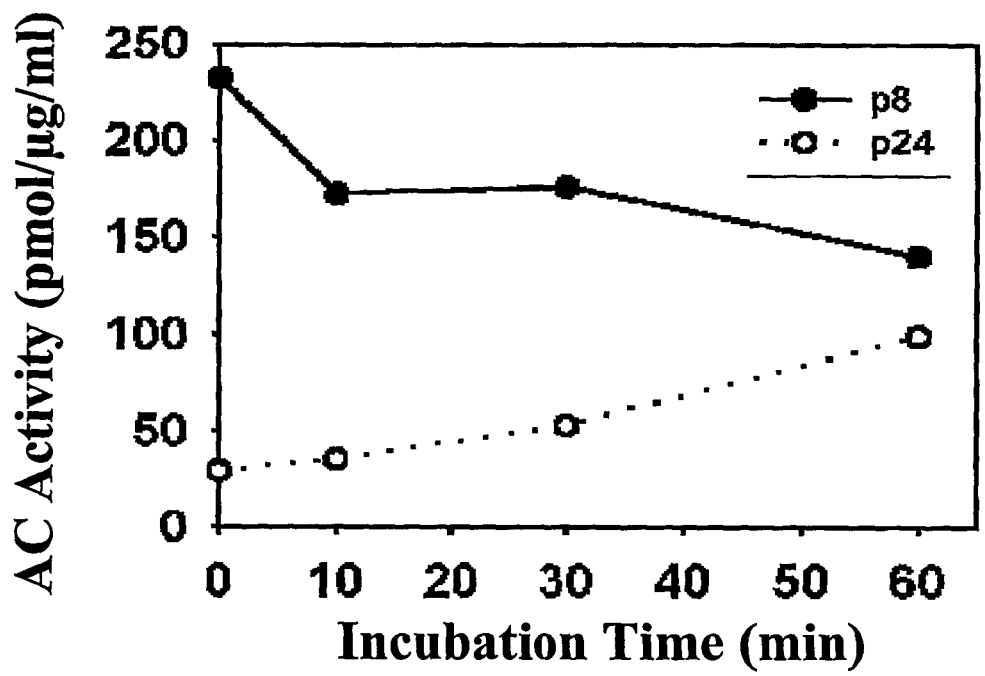
B
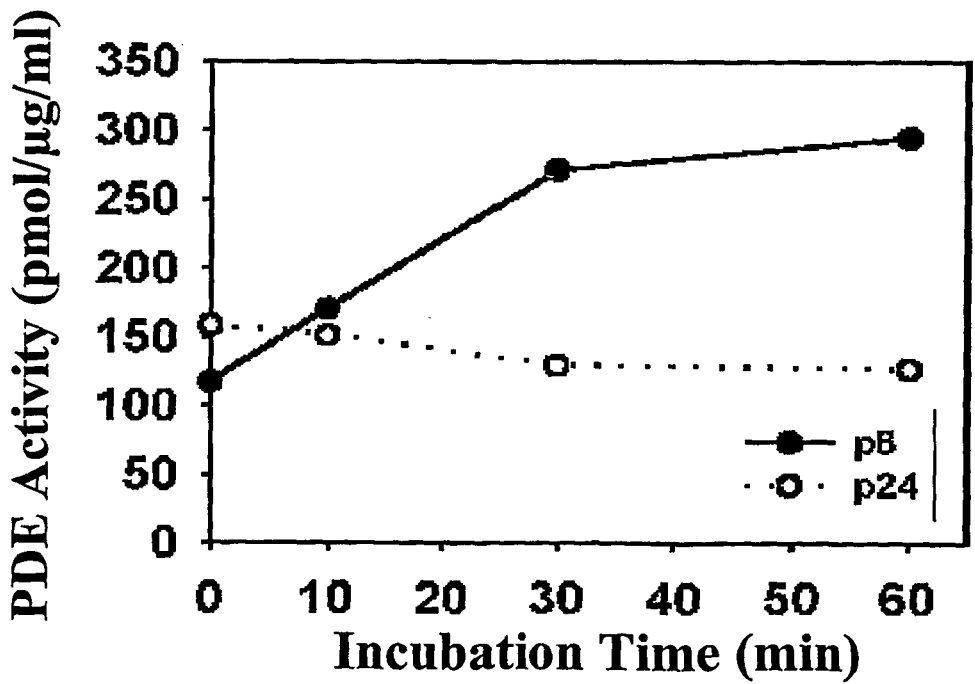

Fig. 12
A
|  | R1 | R2 | R3 | R4 |
|---|---|---|---|---|
| Pa 7 : | 12 | 8 | 4 | 0 |
| Pa 27: | 0 | 4 | 8 | 12 |
 EDG-1
 EDG-2
 EDG-4
 EDG-7
B
|  | Mean count over background | | | |
|---|---|---|---|---|
|  | R1 | R2 | R3 | R4 |
| EDG-1 | 39.1 | 37.5 | 35.0 | 38.5 |
| EDG-2 | 93.9 | 79.1 | 68.3 | 53.2 |
| EDG-4 | 33.9 | 36.5 | 37.3 | 35.1 |
| EDG-7 | 55.4 | 48.7 | 39.6 | 23.2 |

Fig. 14
A Adenylyl Cyclase
| Y O | Y O | Y O | Y O |
|---|---|---|---|
| ACIV | ACII | ACVI | ACIX |
B Phosphodiesterase
| Y O | Y O | Y O | Y O | Y O |
|---|---|---|---|---|
| 1A/B | 1C | 3A | 4B | 4C |
C Protein Kinase A
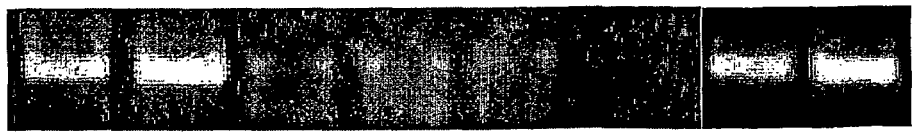
| Y O | Y O | Y O | Y O |
|---|---|---|---|
| RIα | RIβ | RIIα | Cα |

Fig. 16
A
Pa 10
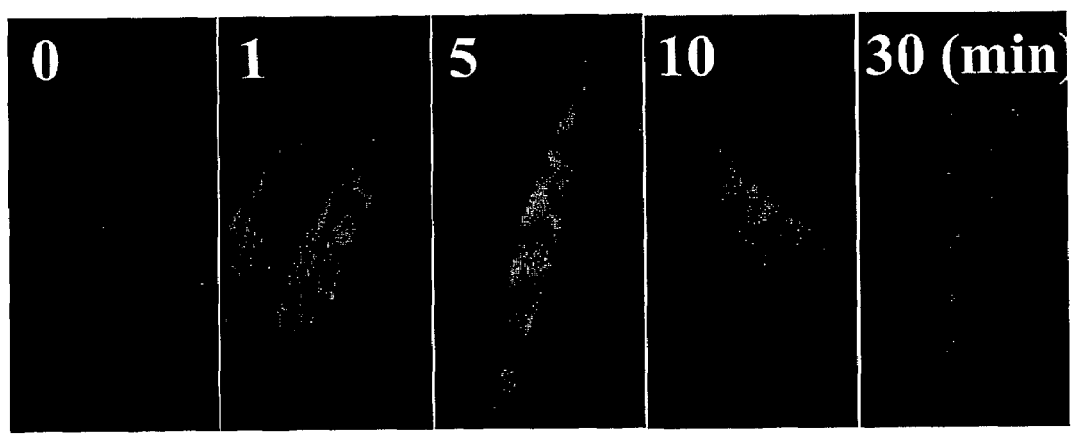
B
Pa 29
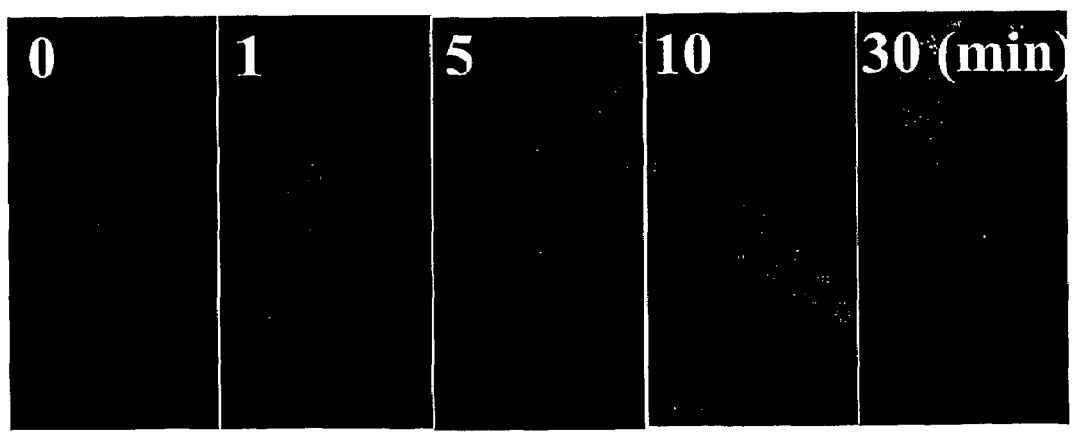

Fig. 18
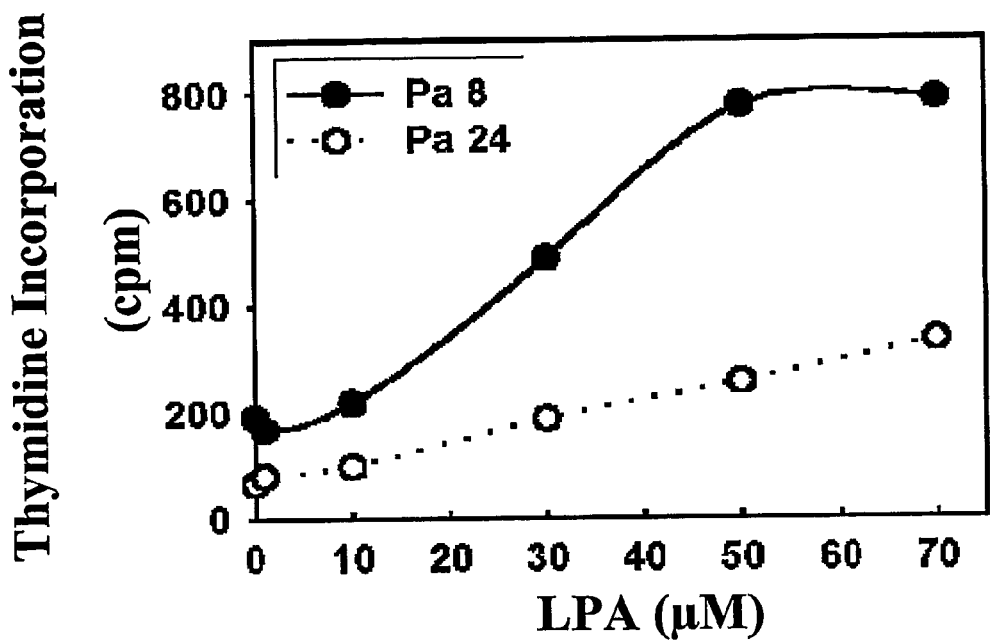
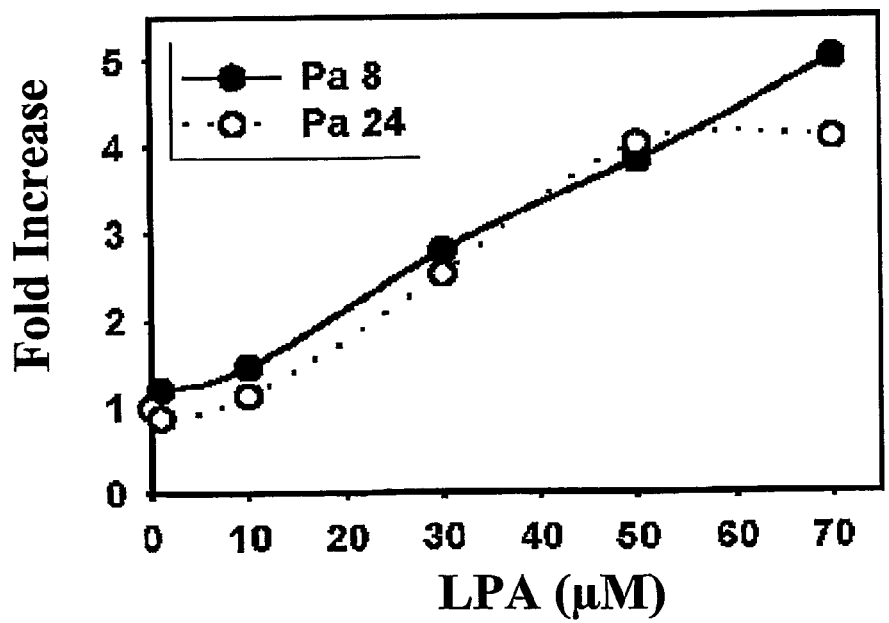

Fig. 19
A
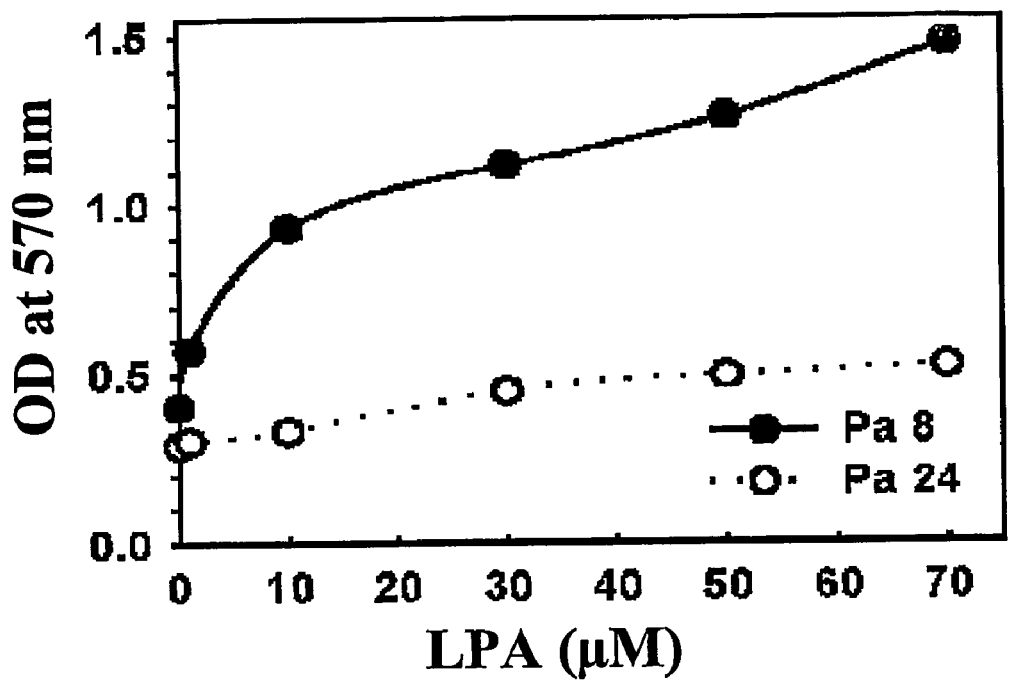
B
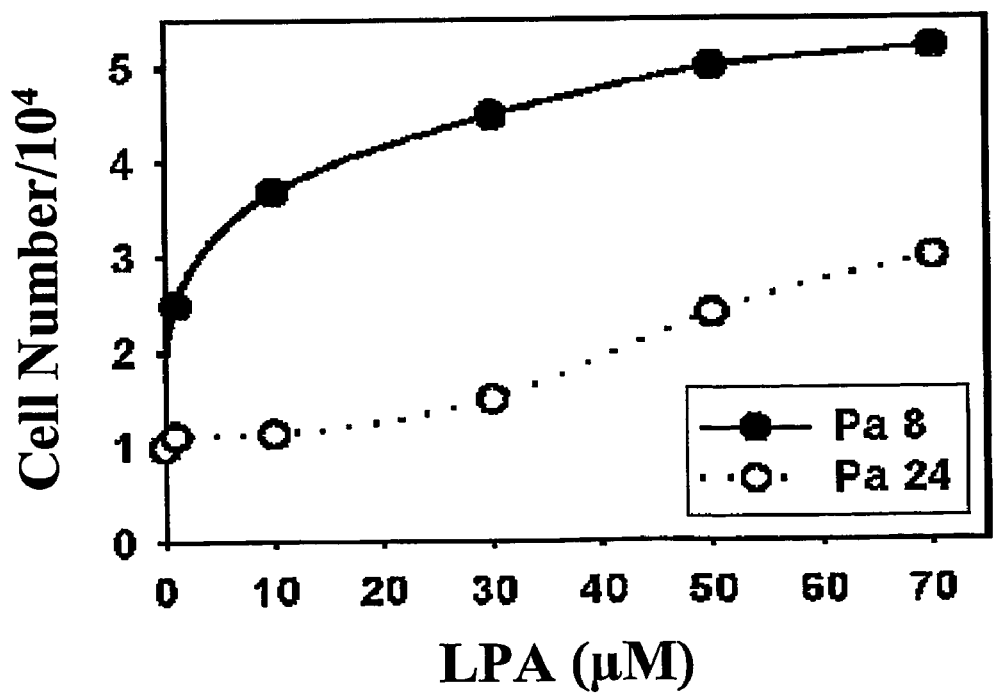

SIGNALS AND MOLECULAR SPECIES INVOLVED IN SENESCENCE

BACKGROUND OF THE INVENTION

1. Field of the Invention

The present invention relates to signals or molecular species involved in senescence and particularly, to signals or molecular species involved in cellular senescence and their use.

2. Description of the Related Art

Cellular senescence plays an important role in complex biological processes, including development, aging, and tumorigenesis, and many attempts have been made to understand some of its fundamental features (Peacocke and Campisi, 1991; Smith and Pereira-Smith, 1996). One of the hallmarks of cellular senescence is the hyporesponsiveness to the growth factors and mitogens.

Age-related quantitative and qualitative alterations in growth factor receptors may account, at least in part, for the diminished responsiveness of senescent cells to growth factors. The decreased numbers of high and low affinity epidermal growth factor (EGF) receptors during serial cultivation in vitro have been reported in human omental microvascular endothelial cells (Matsuda et al., 1992), and the diminished responsiveness to the EGF of particular chondrocytes derived from old animals also seems to be ascribed to a reduction in the number of EGF receptors (Ribault et al., 1998). Age-related reductions in the numbers of PDGF (platelet-derived growth factor) binding sites or PDGF receptors have also been demonstrated in several cell systems including human smooth muscle cells (Mori et al., 1993; Aoyagi et al., 1995).

In contrast, some senescent cells in culture retain functional growth factor receptor systems and have normal numbers of receptors for growth factors with normal binding affinity (Paulsson et al., 1986; Gerhard et al., 1991; Hensler and Pereira-Smith, 1995; Park et al., 2000). In these cases, post-receptor signal transduction pathways in cellular senescence could be responsible for the attenuated responsiveness to growth factors. Upregulation of caveolin and/or the down-regulation of amphiphysin seems to account for the unresponsiveness of senescent fibroblasts to EGF stimulation (Park et al., 2000, 2001). Defects in calcium-phospholipid-dependent protein kinase C (PKC) pathway have also been suggested to be involved in the mitogenic defect of senescent cells (Pascale et al., 1998; Venable and Obeid, 1999). Since phosphatidylcholine-specific phospholipase D (PLD) is activated by PKC and followed by the action of phosphatidic acid, phosphohydrolase results in delayed and more sustained diacylglycerol formation, which might be responsible for the sustained activation of PKC, the activity of PLD could be altered during the aging process. Indeed, Venable et al. (1994) demonstrated a defect in the serum-stimulated PLD/PKC pathway during cellular senescence.

In contrast to previous reports demonstrating a decrease in agonist-stimulated signaling events, some reports have shown an increase in the signaling events. Bradykinin increases $IP_3$ formation in fibroblasts from normal aged and Alzheimer donors (Huang et al., 1991) and PLD activity in human senescent fibroblasts (Meacci et al., 1995) more so than in young counterparts. Human lymphocytes showed elevated mitogen-induced $Ca^{2+}$ responses after exposure to beta-amyloid, the main component of senile plaques in Alzheimer disease (Eckert et al., 1994). These results suggest that the effect of aging on signaling events could be agonist-specific.

PDGF transfers a mitogenic signal via a plasma membrane-bound receptor possessing the activity of protein tyrosine kinase, while lysophosphatidic acid (LPA) acts as an extracellular messenger through guanine nucleotide binding protein (G-protein). Since both PDGF and LPA elicit the same signaling events, including the mobilization of intracellular $Ca^{2+}$, actin polymerization and phosphatidic acid production in human diploid fibroblasts, we compared the responsiveness of senescent or near-senescent cells to two different major mitogenic agonists, PDGF and LPA.

Meanwhile, lysophosphatidic acid (LPA) is a lipid mediator with diverse biological activities, including changes in cell shape, chemotaxis, proliferation, and differentiation (Moolenaar et al., 1997; An et al., 1998c). LPA is generated by phospholipase cleavage of membrane phospholipids from stimulated cells, especially activated platelets (Gaits et al., 1997). The intracellular biochemical signaling events that mediate the effects of LPA include increases in cytoplasmic calcium concentration, stimulation of phospholipases, activation of phosphatidylinositol 3-kinase, the Ras-Raf-MAP kinase cascade, and inhibition of adenylyl cyclase (AC) (Moolenaar et al., 1997). Recently, cell surface G-protein-coupled receptors for LPA were identified as a family of endothelial cell differentiation genes (EDGs) (LPA receptors reviewed in Contos et al., 2000; Fukushima et al., 2001). The major members of the EDG family interacting with LPA were shown to be EDG-2 (Hecht et al., 1996), EDG-4 (An et al., 1998a), and EDG-7 (Bandoh et al., 1999). LPA is also a low affinity agonist for EDG-1 (Lee et al., 1998).

Specific response of the G-protein-coupled receptor to a ligand might be possible only when appropriate G-proteins are coupled to the receptor (Figler et al., 1996; Moolenaar, 1997). EDG-2 is coupled to pertussis toxin-sensitive Gi, whereas EDG4 is coupled to both Gi and Gq (An et al., 1998), and EDG7 to a pertussis toxin-insensitive G-protein(s), possibly Gq (Bandoh et al., 1999; Im et al., 2000). Gq protein could mediate inositol 1,4,5-trisphosphates ($IP_3$) production and subsequent $Ca^{++}$ mobilization, whereas Gi could mediate the inhibition of AC. This complex linkage of LPA-signaling system with a variety of factors suggests the possibility of functional deterioration in age-dependent manner.

Cellular cAMP can be synthesized by activated AC and hydrolyzed by the cyclic nucleotide phosphodiesterases (PDE). An increase in the cAMP content results in the activation of cAMP-dependent protein kinase (PKA), which phosphorylates cellular proteins, regulates gene expression by activating cAMP response element binding protein (CREB), and thus results in numerous cellular responses including cell proliferation, differentiation, metabolism, and neuronal functions (Taussig and Gilman, 1995).

Previously, it was reported that PGE1-induced cAMP accumulation and subsequent phosphorylation of CREB by protein kinase A was markedly attenuated in senescent cells (Chin et al., 1996). However, cAMP signaling induced by forskolin or interferon-γ-inducible protein-10 (IP-10), is relatively maintained in senescent human diploid fibroblasts Hs68 (Shiraha et al., 2000). Rather enhanced cAMP stimulation was observed in late passage-human embryonic lung fibroblasts treated with serum (Polgar et al., 1978) and in senescent IMR-90 lung fibroblasts treated with isoproterenol (Ethier et al., 1992). While the response in VSMC cultured from the older rats was actually increased compared to the VSMC cultured from the younger rats, there was a reduction of cAMP response to isoproterenol in fibroblasts cultured from the older rats (Chin and Hoffman, 1991). These results suggest that the effect of aging on cAMP signaling events could be agonist- and cell-specific.

The patent applications related to nucleic acid and proteins associated with aging process, disclosed in WO 99/52929 and WO 01/23615.

As described above, a variety of theories have been proposed, there remains a need of more evident elucidation for cellular senescence, a need of specific biomarker for identifying senescent cell, and a need of biomolecule for modulating cellular senescence.

In particular, the prospect of reversing senescence and restoring normal physiological function has an importance in certain diseases associated with senescence, for example, Werner Syndrome and Hutchinson-Gilford Syndrome.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

Under such situation, the present inventors have made intensive studies to elucidate signals and molecular species involved in senescence, and as a result, have revealed novel signals and molecular species useful in detecting senescence. Surprisingly, some molecular species has been found to be useful in modulating cellular senescence.

Accordingly, it is an object of this invention to provide a method for detecting a senescent cell.

It is another object of this invention to provide a composition for modulating cellular senescence.

It is still another object of this invention to provide a method for modulating cellular senescence in a patient in need thereof.

It is further object of this invention to provide a method for identifying a substance affecting the senescence of a cell.

Other objects and advantages of the present invention will become apparent from the detailed description to follow taken in conjugation with the appended claims and drawings.

BRIEF DESCRIPTION OF THE DRAWINGS

FIG. 1 represents differential changes in growth factor-stimulated calcium release in senescent fibroblasts. Presenescent (passage 7: A and C) and senescent (passage 27: B and D) fibroblasts were grown on coverslips, serum-starved, and incubated with 4 µM fluo-3-AM in serum-free medium for 40 min. The stained cells were treated with 50 ml of platelet-derived growth factor (A and B) or 1 µg/ml of lysophosphatidic acid (C and D) via a micro-perfusion system for the real-time measurement of signaling molecules, and laser scanning confocal microscopy. The scanned images were analyzed for changes in intracellular $Ca^{2+}$ at the single cell level and results expressed as relative fluorescence intensity (RFI).

FIG. 5 represents reduction of growth factor-induced thymidine incorporation in near-senescent fibroblasts. Subconfluent presenescent (passage 8, Pa 8) and near-senescent (passage 24, Pa 24) fibroblasts were serum-starved for 2 days and treated with 10-200 ng/ml of platelet-derived growth factor (PDGF), or 1-70 µg/ml of lysophosphatidic acid (LPA) for 16 hrs. The amount of [$^3$H]thymidine incorporated into DNA over 4 hrs was measured as described. The data represents an average of 3 counts in cpm. A representative experiment of the three is presented in A. Fold increase over the untreated control was calculated and plotted in B.

FIG. 7 demonstrates changes in the levels of phospholipase C-γ1 and platelet-derived growth factor receptor proteins during the aging process. Presenescent (Passage 6, 8, or 10: Pa 6, Pa 8, Pa 10), intermediate (passage 18, Pa 18), and near-senescent cells (Passage 25 or 27: Pa 25, Pa 27) were lysed in a lysis buffer containing 1% Igepal CA630 non-ionic detergent and the same amounts of protein in the total cell lysates were analyzed by 8% SDS-PAGE and Western blotting using polyclonal anti-phospholipase C-γ1 (PLC-γ1; A) or anti-platelet-derived growth factor receptor A/B antibodies (PDGFR: B). The major platelet-derived growth factor receptor type B in fibroblasts was visualized using an ECL detection system.

FIG. 8 represents changes in the levels of protein kinase Cs and phospholipase D1 proteins during the aging process. Presenescent (passage 6 or 8: Pa 6, Pa 8), intermediate (passage 18: Pa 18), and near-senescent cells (Passage 25 or 27: Pa 25, Pa 27) were lysed in a lysis buffer containing 1% Igepal CA630 non-ionic detergent. To determine the level of protein kinase Cs, the same amounts of protein in the total cell lysates were analyzed by 10% SDS-PAGE and by Western blotting using polyclonal anti-PKCs antibodies (PKCs: A). Phospholipase D1 was immunoprecipitated from the cell lysate (0.5 mg of protein per ml) using polyclonal anti-phospholipase D1 antibodies and analyzed by 8% SDS-PAGE and Western blotting using anti-phospholipase D1 antibodies. The phospholipase D1 protein band and an unknown nonspecific band (p15) were visualized by using an ECL detection system (PLD1: B).

FIG. 9 represents LPA-induced alteration of cellular cAMP content in presenescent and near-senescent fibroblasts. Subconfluent presenescent (passage 8, Pa 8) and near-senescent (passage 24, Pa 24) fibroblasts were serum-starved for 2 days and treated with LPA: A, 1-70 μg/ml LPA for 30 min; B, 30 μg/ml LPA for the indicated times. The level of cAMP in the acid extracts was measured by cAMP binding assay. The data represents an average of triplicate experiments.

FIG. 10 represents LPA-dependent PKA activity and CREB phosphorylation in presenescent and near-senescent fibroblasts. Subconfluent presenescent (passage 8, Pa 8) and near-senescent (passage 24, Pa 24) fibroblasts were serum-starved for 2 days and treated with 30 μg/ml LPA for the indicated times. The PKA activity (A) was determined in cell homogenates with kemptide and [$\gamma^{32}$P]ATP as substrates. The radioactivity incorporated into kemptide was measured by a beta-counter and the enzyme activity was calculated as pmol/min/mg protein. The data represents an average of triplicate experiments. The level of phospho-CREB (B) was measured by Western blot analysis using an anti-phospho-CREB antibody.

FIG. 11 demonstrates LPA-dependent adenylyl cyclase and phosphodiesterase activity in presenescent and near-senescent fibroblasts. Subconfluent presenescent (passage 8, Pa 8) and near-senescent (passage 24, Pa 24) fibroblasts were serum-starved for 2 days and treated with 30 μg/ml LPA for the indicated times. The activities of adenylyl cyclase (A) and phosphodiesterase (B) were determined in the fresh membranes and total cell lysates as described in Materials and Methods. The enzyme activities were calculated as pmol/μg/min. The data represents an average of triplicate experiments.

FIG. 12 represents differential changes in the mRNA levels of LPA receptors during the aging process. Total RNA was isolated from the presenescent (Pa 7) and near-senescent cells (Pa 27) using an acid guanidinium thiocyanate phenol-chloroform extraction method and the mRNA levels were compared by semi-quantitative RT-PCR, as described in Materials and Methods. The RNA mixtures (R1-R4) containing 2 μg of total RNA in 12 μl volume were reverse transcribed and amplified by PCR. RT-PCR products of the LPA receptors (EDG-1, 2, 4, 7) were separated on 1.2% agarose gel, photographed (A), and densitometrically analyzed (B). This experiment was performed three times and similar results were observed. The result of a typical experiment is shown.

Figure 13:
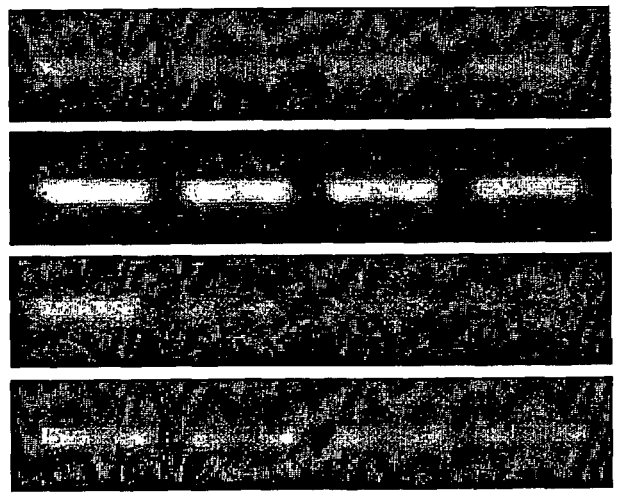

FIG. 13 demonstrates differential changes in the mRNA levels of G proteins during the aging process. Total RNA from the presenescent (Pa 7) and near-senescent cells (Pa 27) was isolated. RT-PCR products of Gq and Gis (Gi1, Gi2, Gi3) were separated on 1.2% agarose gel, photographed (A), and densitometrically analyzed (B). This experiment was performed three times and similar results were obtained. The result from a typical experiment is shown.

FIG. 14 represents expression of the AC, PDE, and PKA isoform mRNAs in presenescent and near-senescent human diploid fibroblasts. Total RNA was isolated from the presenescent (Pa 9, Y) and near-senescent cells (Pa 28, O) using an acid guanidinium thiocyanate phenol-chloroform extraction method and the mRNA levels were compared by semi-quantitative RT-PCR, as described in Materials and Methods. The RNA mixtures (R1-R4) containing 2 μg of total RNA in 12 μl volume were reverse transcribed and amplified by PCR. RT-PCR products of the AC isoforms were separated on 1.2% agarose gel, photographed (A), and densitometrically analyzed (B). This experiment was performed three times and similar results were observed. The result of a typical experiment is shown.

Figure 15:
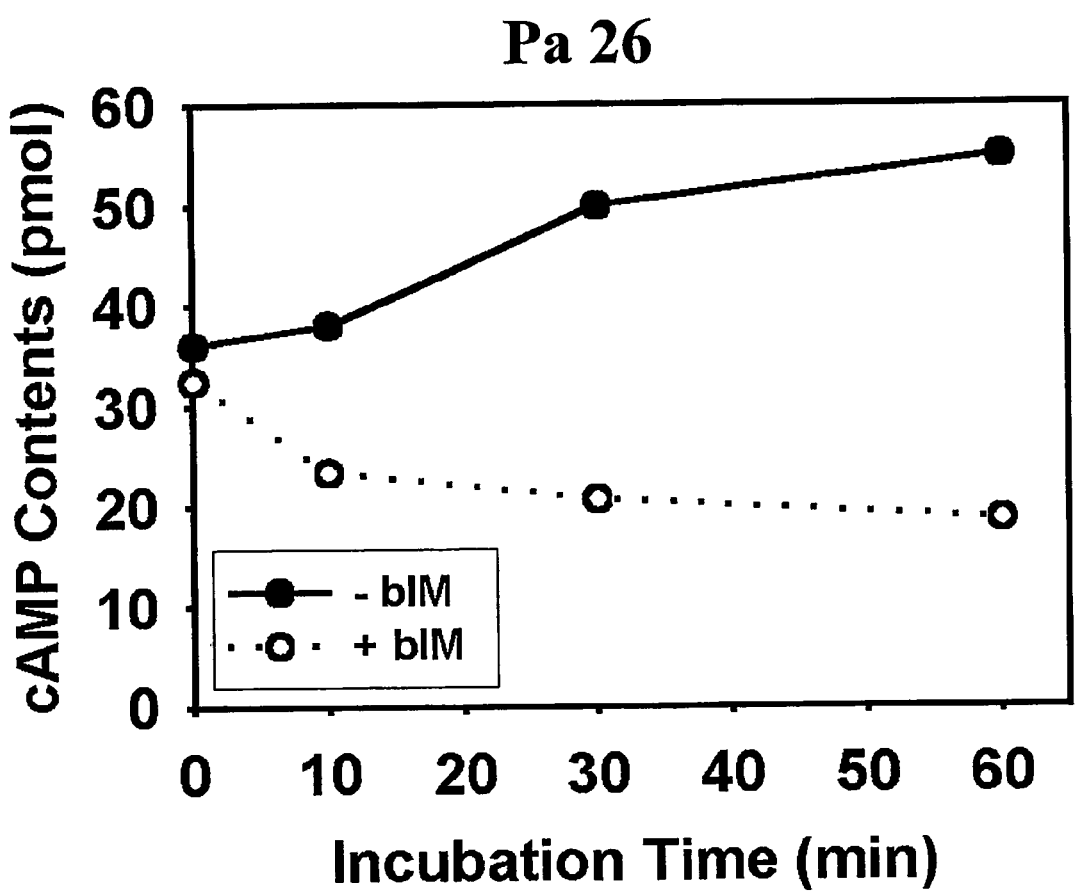

FIG. 15 shows alteration of the cAMP content by LPA in the presence of PKC inhibitor. Subconfluent near-senescent (passage 26, Pa 26) fibroblasts were serum-starved for 2 days and treated with 30 μg/ml LPA for the indicated times in the absence or presence of 10 μM PKC inhibitor bisindolylmaleiamide (bIM). The level of cAMP in the acid extracts was measured by cAMP binding assay. The data represents an average of triplicate experiments.

FIG. 16 represents PKC activation by LPA in presenescent and near-senescent human diploid fibroblasts. Subconfluent presenescent (passage 10, Pa 10) and near-senescent (passage 29, Pa 29) fibroblasts were serum-starved for 2 days and treated with 30 μg/ml LPA for the indicated times. PKC activation was indicated by aggregation and translocation of PKC proteins into the plasma membrane. PKC-α was detected under a confocal microscopy system with polyclonal anti-PKC-α antibodies and FITC-conjugated secondary antibodies.

Figure 17:
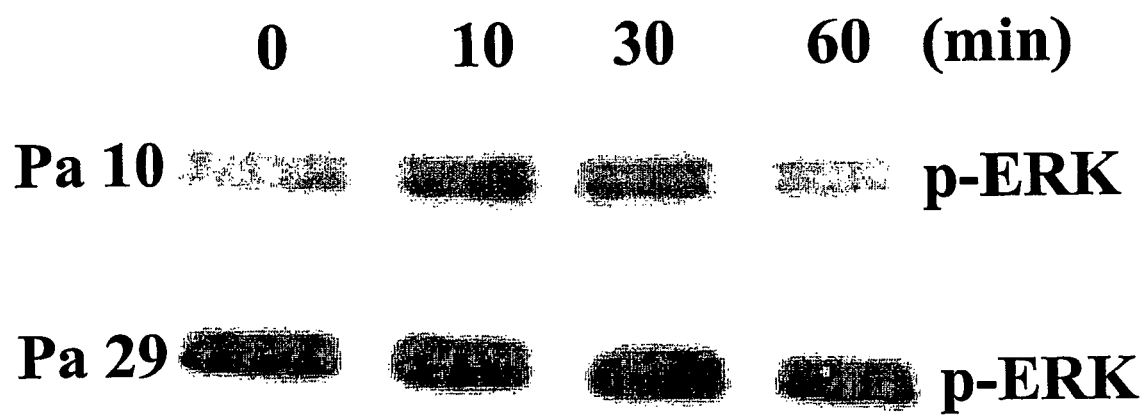

FIG. 17 reveals ERK activation by LPA in presenescent and near-senescent human diploid fibroblasts. Serum-starved presenescent (passage 10, Pa 10) and near-senescent (passage 29, Pa 29) fibroblasts were treated with 30 μg/ml LPA for the indicated times. The level of phospho-ERK in the cytosolic fraction from each cell, as an indication of ERK activation, was measured by Western blot analysis employing anti-phospho-ERK antibody.

FIG. 18 represents changes in LPA-induced thymidine incorporation and cell proliferation in near-senescent fibroblasts versus presenescent fibroblasts. Subconfluent presenescent (passage 8, Pa 8) and near-senescent (passage 24, Pa 24) fibroblasts were serum-starved for 2 days and treated with LPA (1-70 μg/ml) for 16 hrs. The amount of [$^3$H]thymidine incorporated into DNA over 4 hrs was measured as described. The data represents an average of 3 counts in cpm in each independent experiments. A representative experiment of the three is presented in A. Converted fold increase over the untreated control was calculated and plotted in B.

FIG. 19. shows cell proliferation induced by LPA in presenescent and near-senescent human diploid fibroblasts. The optical density at 570 nm was plotted (A). The actual viable cell numbers were plotted (B).

Figure 20:
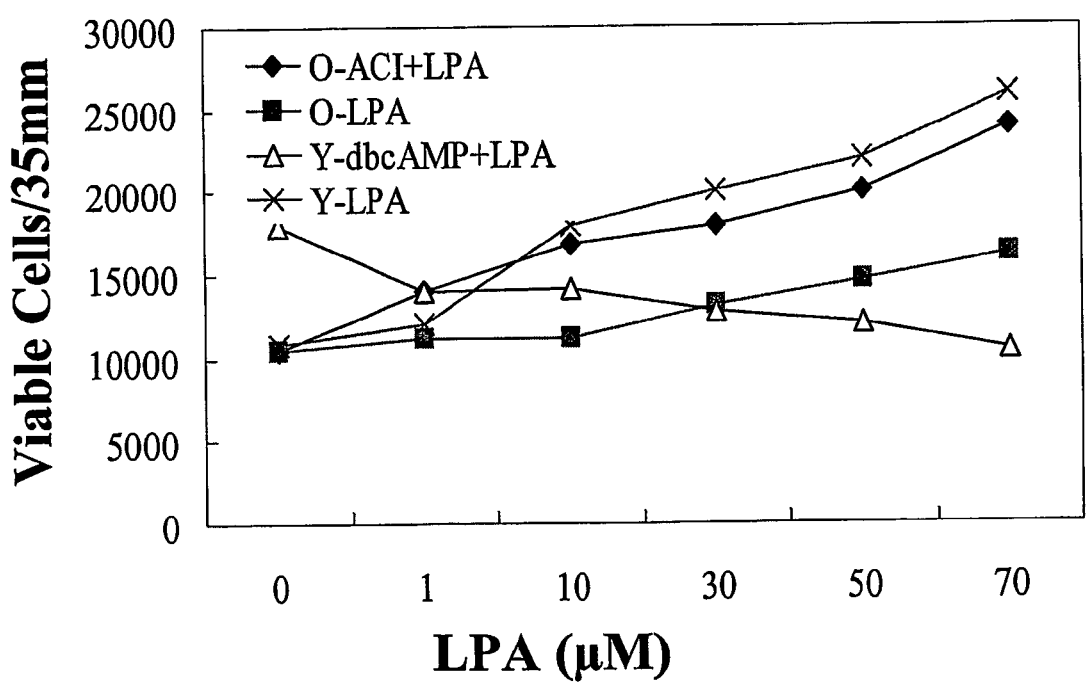

FIG. 20 shows the results of viable cell counting depending on adenylyl cyclase inhibitor (ACI) and/or LPA in senescent cell. O and Y denote old and young cell, respectively.

Figure 21:
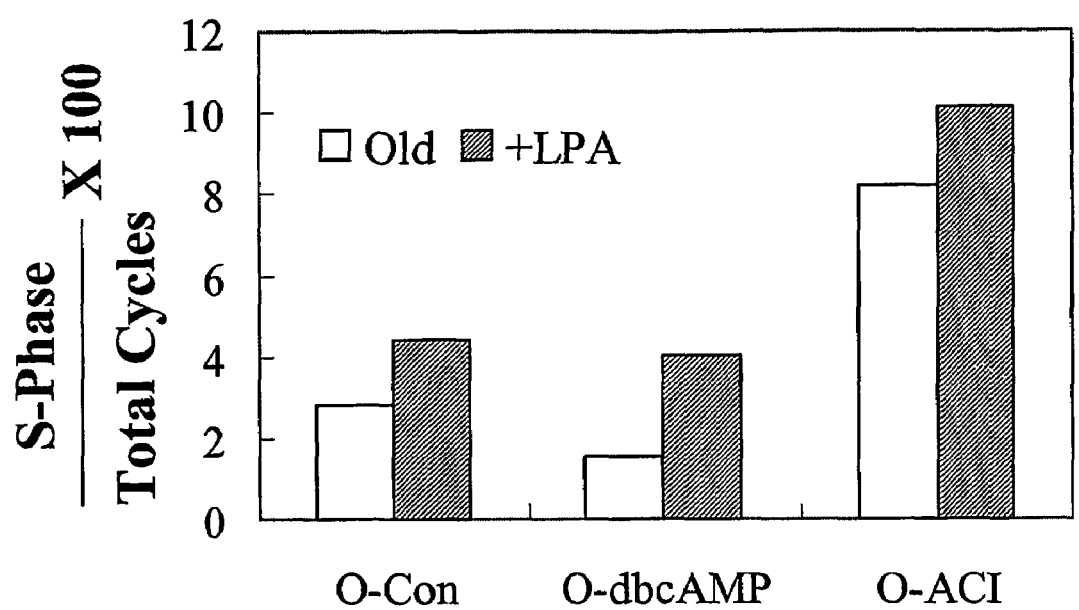

FIG. 21 represents the results of FACS analysis evaluating the effect of LPA on cell cycle progression in senescent cells in connection with the affection of cAMP control. Con denotes control group and ACI is adenylyl cyclase inhibitor.

DETAILED DESCRIPTION OF THIS INVENTION

The present invention, in principle, is directed to novel signals and molecular species involved in cellular senescence. The signals and molecular species can indicate cellular senescence in a reliable manner.

I. Methods for Detecting a Senescent Cell and Identifying a Substance Affecting Cellular Senescence In one aspect of this invention, there is provided a method for detecting a senescent cell, which comprises measuring a relative alteration to young cell in a signal or molecular species involved in signal transduction, wherein the alteration in signal or molecular species is one or more selected from the group consisting of: (a) a reduction in $Ca^{2+}$ oscillation; (b) a reduction in expression of F-actin; (c) a reduction in activity of phospholipase C; (d) a reduction in activity of phospholipase D; (e) a reduction in expression or phosphorylation of platelet-derived growth factor receptor; (f) a reduction in phosphorylation of phospholipase C-γ1; (g) a reduction in expression of phospholipase D1; (h) a reduction in expression of EDG (endothelial cell differentiation gene)-2; (i) a reduction in expression of EDG-7; (j) a reduction in expression of Gi1; (k) a reduction in expression of Gi2; (l) a reduction in expression of Gi3; (m) an increase in activity or expression of adenylyl cyclase; (n) a reduction in activity or expression of phophodiesterase; (o) an increase in activity of protein kinase C; (p) an increase in activity or expression of protein kinase A; (q) an increase in phosphorylation of CREB; and (r) an increase in cAMP content.

In another aspect of this invention, there is provided a method for identifying a substance affecting the senescence of a cell, which comprises the steps of: (a) culturing the cell in the presence of the substance to be tested; and (b) measuring a relative alteration to young cell in a signal or molecular species involved in signal transduction, wherein the alteration in signal or molecular species is one or more selected from the group consisting of: (a) a reduction in $Ca^{2+}$ oscillation; (b) a reduction in expression of F-actin; (c) a reduction in activity of phospholipase C; (d) a reduction in activity of phospholipase D; (e) a reduction in expression or phosphorylation of platelet-derived growth factor receptor; (f) a reduction in phosphorylation of phospholipase C-γ1; (g) a reduction in expression of phospholipase D1; (h) a reduction in expression of EDG-2; (i) a reduction in expression of EDG-7; (j) a reduction in expression of Gi1; (k) a reduction in expression of Gi2; (l) a reduction in expression of Gi3; (m) an increase in activity or expression of adenylyl cyclase; (n) a reduction in activity or expression of phophodiesterase; (o) an increase in activity of protein kinase C; (p) an increase in activity or expression of protein kinase A; (q) an increase in phosphorylation of CREB; and (r) an increase in cAMP content.

The present methods employ signals or molecular species (e.g., ions and proteins) involved in signal transduction. In the present methods, the level of signal or molecular species, which is measured for unknown cell sample is compared to that in young cell. The reduced or increased level of signal or molecular species, which is relative to young cell, provides detection of senescent cell and identification of substance affecting cellular senescence.

The term used herein "senescence" has the same meaning as "aging". The term used herein "near senescent" refers to cellular state substantially identical to senescent state. For example, the near senescent cell exhibits the cessation of cell growth and senescence-like morphological changes. The term "presenescent" along with cell means young cell. Unless otherwise defined, all technical and scientific terms used herein have the same meaning as commonly understood by one of ordinary skill in the art to which this invention belongs. For example, the terms used herein may be found in Benjamin Lewin, *Genes VII*, published by Oxford University Press (2000); and Kendrew et al., *The Encyclopedia of Molecular Biology*, published by Blackwell Science Ltd. (1994).

According to the preferred embodiment of this invention, the signals or molecular species of (a)-(g) are involved in signal transduction triggered by platelet-derived growth factor (hereinafter referred to as PDGF). In the preferred embodiment, the signals or molecular species of (h)-(r) are involved in signal transduction triggered by lysophosphatidic acid (hereinafter referred to as LPA).

According to the preferred embodiment, the cell suitable for this invention is derived from mammalian cell such as human cell. More preferably, the cell used in this invention is fibroblast.

In the case that the activity or expression of adenylyl cyclase is measured for detecting senescent cell, it is preferred to target a specific isoform thereof including adenylyl cyclase II, adenylyl cyclase IV and adenylyl cyclase VI. In addition, in the case that the expression of phophodiesterase is measured for detecting senescent cell, it is preferable to target phophodiesterase 4B. It is preferred to target the protein kinase A subunits Cα, RIα or RIβ subunit, in the case that the expression of protein kinase A is measured for detecting senescent cell.

In the specific example of the present method, the measuring step is conducted by western blotting method. The general procedures of western blotting are disclosed in Peter B. Kaufman et al., *Molecular and Cellular Methods in Biology and Medicine*, 108-121, CRC Press. Antibodies for western blotting may be obtained as methods known to those skilled in the art (*Antibodies: A Laboratory Manual*, Cold Spring Harbor Laboratory (1988)). The antibody may be polyclonal or monoclonal antibody. Monoclonal antibody may be readily prepared through use of well-known techniques, such as those exemplified in U.S. Pat. No. 4,196,265. The antibody may be labeled, for more convenient detection, with radioactive, fluorescent, biological or enzymatic tags or labels.

With comparing the western blotting band derived from senescent cell to one derived from young cell, the senescence can be easily detected. Moreover, the present method may be carried out in a quantitative manner. For example, the bands resulted from western blotting may be transformed to quantitative data with densitometer.

In a specific example of the present methods, the measuring step particularly for expression level of certain protein, can be performed by northern blotting or RT-PCR (reverse transcription-polymerase chain reaction), preferably RT-PCR. The general procedures of northern blotting method are disclosed in Peter B. Kaufma et al., *Molecular and Cellular Methods in Biology and Medicine*, 102-108, CRC Press. In addition, the general procedures of RT-PCR are disclosed in J. Sambrook, et al., *Molecular Cloning*, 2:8.86-8.95, CSHL Press (2001).

II. Method and Composition for Modulating Cellular Senescence

In still another aspect of this invention, there is provided a method for modulating cellular senescence comprising treating a senescent cell with the effective amount of an inhibitor of adenylyl cyclase, an inhibitor of protein kinase A, an inhibitor of protein kinase C or an activator of Gi protein.

In addition, the present invention provides a method for modulating cellular senescence in a patient in need thereof, comprising administering to the patient the effective amount of an inhibitor of adenylyl cyclase, an inhibitor of protein kinase A, an inhibitor of protein kinase C or an activator of Gi protein.

Such proteins are involved in Gi-mediated signal transduction in vivo.

The present inventors have discovered that the activity or expression of proteins, which are involved in Gi-mediated signal transduction, can be adjusted to modulate cellular senescence.

Although the present method can be applied to any senescent cell, the more significant cells in therapeutics involve (a) cells with replicative capacity in the central nervous system, including astrocytes, endothelial cells, and fibroblasts which play a role in such age-related diseases as Alzheimer's disease, Parkinson's disease, Huntington's disease, and stroke; (b) cells with finite replicative capacity in the integument, including fibroblasts, sebaceous gland cells, melanocytes, keratinocytes, Langerhan's cells, and hair follicle cells which may play a role in age-related diseases of the integument such as dermal atrophy, elastolysis and skin wrinkling, sebaceous gland hyperplasia, senilelentigo, graying of hair and hair loss, chronic skinulcers, and age-related impairment of wound healing; (c) cells with finite replicative capacity in the articular cartilage, such as chondrocytes and lacunaland synovial fibroblasts which play a role in degenerative joint disease; (d) cells with finite replicative capacity in the bone, such as osteoblasts, bone marrow stromal fibroblasts, and osteoprogenitor cells which play a role in osteoporosis; (e) cells with finite replicative capacity in the immune system such as B and T lymphocytes, monocytes, neutrophils, eosinophils, basophils, NK cells and their respective progenitors, which may play a role in age-related immune system impairment; (f) cells with a finite replicative capacity in the vascular system including endothelial cells, smooth muscle cells, and adventitial fibroblasts which may play a role in age-related diseases of the vascular system including atherosclerosis, calcification, thrombosis, and aneurysms; and (g) cells with a finite replicative capacity in the eye such as pigmented epithelium and vascular endothelial cells which may play an important role in age-related macular degeneration.

In further aspect of this invention, there is provided a composition for modulating cellular senescence of a senescent cell comprising the effective amount of an inhibitor of adenylyl cyclase, an inhibitor of protein kinase A, an inhibitor of protein kinase C or an activator of Gi protein.

Based on the novel findings above described, the present inventors have researched an effective target for modulating cellular senescence. As a result, adenylyl cyclase, protein kinase A, protein kinase C and Gi protein has been elucidated to the suitable target for modulating cellular senescence. As described above, the targets exhibit the increased or reduced expression and/or activity in senescent cell relative to young cell, i.e., presenescent cell.

In the present invention, the suitable inhibitor of adenylyl cyclase may not be specifically limited and includes any one known to those skilled in the art. For instance, the inhibitor includes 2',5'-dideoxyadenosine, cis-N-(2-phenylcyclopentyl)azacyclotridec-1-en-2-amine, and 9-(tetrahydro-2'-furyl) adenine. These inhibitors are commercially available from Calbiochem. The effective amount of adenylyl cyclase inhibitor for modulating cellular senescence is from 1 to 500 µM.

The inhibitor of protein kinase A suitable in the present invention, includes adenosine 3',5'-cyclic phosphorothiolate, 8-bromo-adenosine 3',5'-cyclic monophosphorothioate, 4-cyano-3-methylisoquinoline, 1-(5-isoquinolinesulfonyl)-2-methylpiperazine, N-[2-(methylamino)ethyl]-5-isoquinolinesulfonamide, isoquinolinesulfonamide, N-(2-aminoethyl)-5-isoquinolinesulfonamide, N-[2-((p-bromocinnamy) amino)ethyl]-5-isoquinolinesulfonamide and (5-isoquinolinesulfonyl)piperazine (commercially available from Calbiochem), but not limited to.

The non-limiting inhibitor of protein kinase C in this invention, includes, but not limited to, 2-[1-(3-dimethylaminopropyl)-1H-indol-3-yl]-3-(1H-indol-3-yl)-maleimide, 2-[1-[2-(1-methylpyrrolidino)ethyl]-1H-indol-3-yl]-3-(1H-indol-3-yl)maleimide, 2-[1-(3-aminopropyl)-1H-indol-3-yl]-3-(1H-indol-3-yl)maleimide, 2,3-bis(1H-indol-3-yl)maleimide and 2,3-bis(1H-indol-3-yl)-N-methylmaleimide (commercially available from Calbiochem). The effective amount of protein kinase A inhibitor for modulating cellular senescence is in the range of 1 to 500 µM. The activator of Gi protein in this invention, includes, but not limited to, $N_6$-cyclopentyladenosine, 5-chloro-$N_6$-adenosine, 2-[p-(2-carboxyethyl) phenethylamino]-5'-N-ethylcarboxamidoadenosine, oxymetazoline, prazosin, 2-[2-[4-(2-methoxyphenyl)-1-piperazinyl]ethyl]-4,4-dimethyl-(2H,4H)-isoquinoline-1,3-dione, cannibinol, MGSA (melanoma growth stimulatory activity; available in Sigma), 3-aminopropylphosphinic acid, galanin, quisqualate, sumatriptan, melatonin, (5,7,8)-(−)-N-methyl-[7-(1-pyrrolidinyl)-1-oxaspiro(4,5)dec-8-yl]benzeneacetamide and pertussis toxin. The effective amount of protein kinase A inhibitor for modulating cellular senescence is in the range of 1 to 500 µM.

According to the preferred embodiment, the cell suitable for this invention is derived from mammalian cell such as human cell. More preferably, the cell used in this invention is fibroblast.

The following specific examples are intended to be illustrative of the invention and should not be construed as limiting the scope of the invention as defined by appended claims.

EXAMPLES

Materials and Methods

Materials

Dulbecco's modified Eagle's medium, platelet-derived growth factor (PDGF) lysophosphatidic acid (LPA), dibutyric cAMP (dbcAMP), and IGEPAL CA630 were from Sigma; fetal bovine serum, antibiotics containing penicillin and streptomycin and superscript II reverse transcriptase kit were from Gibco/BRL Life Technologies, Inc.; polyclonal anti-phospholipase D1 antibodies (Box45-ESTP4 for immunoprecipitation and NC-STP4 for Western blot analysis) were generously donated by Dr. Pangil Suh at Pohang University; polyclonal anti-platelet-derived growth factor (PDGF) type A/B receptor and protein kinase C-α antibodies were purchased from Upstate Biotechnology; polyclonal anti-Gi and Gq antibodies were from Santa Cruz biotechnology; and PCR reagents including Taq polymerase were from Takara. The ECL detection kit, cAMP assay kit, [γ-$^{32}$P]ATP and [$^3$H] myristic acid were from Amersham Pharmacia Biotech. [$^3$H] thymidine from NEN; phosphatidylbutanol from Avanti; Kemptide from UBI; Immobilon PVDF from Millipore; N-(7-Nitrobenz-2-oxa-1,3-diazol-4-yl) phallacidin (NBD-phallacidin) was from Molecular Probes (Eugene, Oreg., USA).

Cell Culture

Foreskin fibroblasts were isolated as described by Boyce and Ham (1983). Cells were cultured in Dulbecco's modified Eagle's medium containing 10% fetal bovine serum and antibiotics. The primary culture contained smaller and more closely packed cells during the early stage of the culture. Cells with less than 10 passage were often considered as presenescent cells. As the cells were passaged, they became larger and they have a slower growth rate at passage 10-20. Cells from over 27 passages were completely growth-arrested and developed characteristic appearance designated previously as replicative senescence (Yeo et al., 2000a and b). In order to confirm that cells were senescent, we either examined the activity of beta-galactosidase or stained with X-gal, a membrane permeable substrate of the enzyme, which produces a blue insoluble product inside of the cells. The number of cells stained with X-gal increased with age and most of cells from passage 27-28 were stained. Cultures of over 23-28 passages have also shown the cessation of cell growth and senescence-like morphological changes, but only 70-80% of cells were stained with X-gal. These were termed "near-senescent". Although the near-senescent cultures were not completely homogeneous, we compared the changes in these cultures to those in presenescent cultures of passage 6-10. In order to determine the growth factor-stimulated signaling events, cells were grown for 1-2 days to 60-70% sub-confluency in the culture medium, and then serum-starved to become quiescent by incubating with serum free medium (SFM) for 2 days. The quiescent cells were treated with various agonists, as described in the figure legends. To label cells, radioactive chemicals were added during the incubation with SFM.

Measurement of Cytosolic Free $[Ca^{2+}]i$ $[Ca^{2+}]i$ was measured using a laser scanning confocal microscope, as described by Junn et al. (2000). Quiescent fibroblasts grown on glass cover slips in a 6-well plate were stained with 4 µM of fluo-3-acetoxymethyl ester (fluo-3-AM) in phenol red-free medium without serum for 40 min and washed three times with the serum-free medium. Stained cells on each cover slip were mounted on a perfusion chamber (MPS-1000, Seoul Engineering, Korea), placed under the confocal laser scanning microscope (Carl Zeiss LSM 410), and scanned every 5 sec with a 488 nm excitation argon laser and a 515 nm long pass emission filter. Growth factors were added to the cells using an automatic pumping system (self-designed). All scanned images were analyzed for $[Ca^{2+}]i$ changes at the single cell level using "Time Series Program" for a real-time measurement of relative fluorescence intensity (RFI) which is installed in the Carl Zeiss LSM 410 confocal system.

Confocal Microscopic Measurement of Actin Polymerization

F-actin was stained as described by Shin et al. (1999). Quiescent cells grown on glass cover slips in multi-well culture plates were treated with agonists for 30 min, and the cells were fixed with 3.7% paraformaldehyde in PBS for 30 min on ice. Following permeabilization with 0.2% Triton X-100 in PBS for 15 min on ice, the cells were stained with 0.165 M NBD-phallacidin in PBS for 30 min at RT. The stained cells were washed three times with PBS for 15 min and the cover slip was mounted on a slide glass with Gelvatol, which was prepared by mixing 100 ml of 23% polyvinyl alcohol in PBS with 50 ml glycerol. The cells were then observed under a confocal fluorescence microscope.

Measurement of Phosphatidylbutanol Formation as an Indication of Phospholipase D Activity Quiescent cells were labeled overnight with [$^3$H]myristic acid (1 µCi/ml) and then washed with PBS. Phosphatidylbutanol formation was measured as described by Yeo et al. (1994). Cells were preincubated with 0.5% (v/v) 1-butanol for 15 min and then treated with agonists for 20 min in the presence of 0.5% 1-butanol. Total lipids were extracted and separated by thin layer chromatography. The band of phosphatidylbutanol was scraped off the plates and its radioactivity was counted in a liquid scintillation cocktail.

Western Blot Analysis

The expression levels of signaling proteins were examined by Western blot analysis, as described previously (Yeo et al., 2000a). Total cell lysates were prepared in a lysis buffer containing 50 mM Tris-HCl, pH 7.5, containing 150 mM NaCl, 2 mM EDTA, 1 mM EGTA, 1 mM $Na_3VO_4$, 10 mM NaF, 1 mM DTT, 1 mM PMSF, 25 µg/ml leupeptin, 25 µg/ml aprotinin, 5 mM benzamidine, and 1% Nonidet P-40. The protein concentrations of the lysates were determined using a BCA protein assay kit, as described by the protocol supplied by the manufacturer. Cell lysates containing equal amounts of protein were resolved by SDS-polyacrylamide gel electrophoresis and transferred onto Immobilon PVDF membranes. The blot was blocked with a blocking solution containing 5% non-fat dry milk and 0.1% Tween 20, and then treated with antibodies in the blocking solution overnight. The blots were washed and further incubated with horseradish peroxidase-conjugated anti-rabbit IgGs (1:5000), and the immune complexes were visualized using an enhanced chemiluminescence (ECL) system, as described by the manufacturer. To examine the level of phospholipase D1/2, the immunoprecipitated protein obtained using 10 µl of anti-phospholipase D1 anti-sera (Box45, ESTP4) was analyzed by Western blot against polyclonal anti-phospholipase D1 antibodies (1:20 dilution of NC STP4 anti-serum).

Measurement of Total Inositol Phosphates

Presenescent and near-senescent cells were serum-starved for 2 days and labeled with 0.5 µCi/ml of myo-[$^3$H]inositol overnight in inositol-free Dulbecco's modified Eagle's medium containing 0.1% bovine serum albumin and antibiotics. The cells were then washed three times with serum-free medium containing 0.1% bovine serum albumin. After preincubating the cells in the medium for 1 h at 37° C., 20 mM of LiCl was added for 10 min prior to incubation with 50 ng/ml of PDGF or 1 µg/ml of LPA. After 20 min, the cells were washed twice with ice-cold phosphate-buffered saline and lysed with 25 mM formic acid. Total inositol phosphates were measured as described previously (Yeo et al., 1994).

Measurement of Cyclic AMP (cAMP) Accumulation

Cells grown on a 12 well-plate were serum-starved by incubating with SFM for 2 days. After the cells were equilibrated in the fresh SFM medium for 1 hour, they were treated with LPA as described in the figure. The reaction was terminated by removing the medium and by adding 2.5 M perchloric acid. The acid extract was stored at −20° C. until use. The acid extract was neutralized with 4.2 M KOH and the cAMP content was determined by competitive binding with [$^3$H] cAMP to the cAMP binding protein, RIα of cAMP-dependent protein kinase, as described by Jang and Juhnn (2001). After the extraction, cells were lyzed with 0.1 N NaOH and analyzed for protein content using the Bradford protein assay reagent. The cAMP content was normalized to the amount of acid-insoluble protein.

Measurement of Adenylyl Cyclase Activity

Cells seeded in a 10-cm culture plate were serum-starved and treated with LPA as described in the figure legends. Cells were harvested and homogenized in ice-cold homogenization buffer containing 0.25 M sucrose, 10 mM Tris-HCl, pH 7.5, 10 mM $MgCl_2$, 2 mM EGTA, and protease inhibitors. Homogenates were centrifuged at 20,000×g at 4° C. for 20 min. Pellets were washed twice with the above buffer, resuspended in 10 mM Tris-HCl, pH 7.4, and 10 MM $MgCl_2$, and the adenylyl cyclase assays were performed as described previously (Jang et al. 2001). The membrane proteins (15 µg/ml) were incubated for 10 min at 30° C. in a reaction mixture (100 µl) containing 40 mM Tris, pH 7.4, 0.2 mM EGTA, 100 mM NaCl, 10 mM $MgCl_2$, 0.5 mM ATP, 5 µg/ml phosphocreatine, 5 IU/ml creatine phosphokinase, 10 µM GTP, and 0.5 mM IBMX. The reaction was stopped by adding 2.5 M perchloric acid. The amount of cAMP generated was determined by cAMP binding assay.

Measurement of Phosphodiesterase Activity

Phosphodiesterase (PDE) assays were performed as described previously (Jang and Juhnn, 2001). 15 µg of cytosolic proteins were incubated in 200 µl of reaction mixture containing 50 mM Tris-HCl, pH 7.4, 3 mM $MgCl_2$, 60 pmol cAMP, 1 mM 5'-AMP for 15 min at 37° C. After the reaction was stopped by adding 2.0 M perchloric acid, the amount of remaining cAMP was determined by cAMP binding assay.

Measurement of Protein Kinase A Activity

LPA-treated cells were harvested and homogenized in ice-cold homogenization buffer containing 0.25 M sucrose, 10 mM Tris-HCl, pH 7.5, 10 MM $MgCl_2$, 2 mM EGTA, and protease inhibitors. Homogenates were centrifuged at 20,000×g at 4° C. for 20 min. Protein kinase A assays were performed as described previously (Yang et al., 1999). The kinase reaction mixture contained 10 μl of substrate cocktail (500 μM Kemptide and 10 μM cAMP), 10 1 of inhibitor cocktail (20 μM PKC inhibitor peptide and 20 μM compound R24571), 10 μl of tissue homogenate, and 10 μl of the mixture containing 0.5 mM ATP, 75 mM $MgCl_2$ and 10 μCi of [$\gamma$-$^{32}$P] ATP (3000 Ci/mmol). After the mixture was incubated for 10 min at 30° C., 25 μl of the mixture was blotted on the P81 paper square. The paper was washed once with 0.75% phosphoric acid and the radioactivity incorporated into Kemptide was quantified on a scintillation counter (Model Tri-Carb 1600 CA, Packard Instrument Company). Samples were assayed in triplicate for each condition. PKI-inhibitable kinase activity was calculated and the data were reported as percent of total PKA activity.

Cell extracts were incubated for 5 min at 30° C. in a kinase reaction buffer with 50 mM Tris, pH 7.5, 10 mM $MgCl_2$, 100 μM ATP, 4 mmol of [$\gamma$-$^{32}$P]ATP, 0.25 mg/ml BSA, and 50 μM of Kemptide (Leu-Arg-Arg-Ala-Ser-Leu-Gly), either alone (control) or in the presence of 1 μM PKI peptide (background), 10 μM cAMP (total activity), or PKI plus cAMP (total background activity). Samples were assayed in triplicate for each condition and the radioactivity incorporated into Kemptide was quantified on a scintillation counter. PKI-inhibitable kinase activity was calculated and the data were reported as percent of total PKA activity.

Semi-Quantitative RT-PCR

Total RNA was extracted from the presenescent and near-senescent cells using an acid guanidinium thiocyanate phenol-chloroform extraction based method (Chomczynski and Sacchi, 1987). In order to compare the relative amounts of mRNA in the presenescent and near-senescent cells, semi-quantitative reverse transcription/polymerase chain reaction (RT-PCR) was performed as described by Nicoletti and Sassy-Prigent (1996). A series of mixtures were prepared by mixing RNA from the presenescent and near-senescent cells as indicated, so that each mixture had the same total amount of RNA (2 μg) in a constant volume (12 μl). The RT reaction was carried out in a final volume of 20 μl using superscript II reverse transcriptase according to the manufacturer's protocol and 4 μl of the final RT product mix was then PCR amplified. The primer sets used were 5'-ATG ATC GAC CGC AAC CTC-3' and 5'-CTT CAA CCT CCC CAT AGC C-3' for $G_{i1}$, 5'-GAT CGA CTT TGC CGA CCC-3' and 5'-TCG TTC AGG TAG TAG GCA GC-3' for $G_{i2}$, 5'-TGG CAG TGC TGA AGA AGG-3' and 5'-GGT CTT CAC TCT CGT CCG-3' for $G_{i3}$ (Takano et al., 1997). The primers used for Gqα were 5'-ATG ACT TGG ACC GTG TAG CCG ACC-3' (sense) and 5'-CCA TGC GGT TCT CAT TGT CTG ACT-3' (antisense) as described by Shah (1999). A DNA fragment corresponding to the third cystosolic loop (i3) of EDG-1 was also amplified by PCR using the primers, 5'-AGA ATC TAC TCC TTG GTC AGG ACT-3' (sense) and 5'-TAC CCG GGT TAC TTG AGC GCC AGC GAC TTC TC-3' (antisense) (Lee et al., 1996). The PCR primers for EDG-2, -4, and -7 were designed based on the unconserved amino acid sequences containing differential transmembrane regions (Bandoh et al., 1999). The EDG-2 primers amplified the region containing TM 1 through TM 3 (360 bp); EDG-4 primers, TM 1 through 5 (582 bp); and EDG-7 primers, TM 1 through 6 (750 bp). The oligonucleotides used were 5'-GGA AAG CAT CTT GCC ACA GAA-3' (sense) and 5'-GCC GGT TGC TCA TCC GTG TGT-3' (antisense) for EDG-2, 5'-GGC AAA GAG CTC AGC TCC CAC-3' (sense) and 5'-CAT GCG CTG CAC TCG CCG CCG-3' (antisense) for EDG-4, and 5'-AAC ACT GAT ACT GTC GAT GAC-3' (sense) and 5'GAC AGT CAT CAC CGT CTT CAT-3' (antisense) for EDG-7. The primers for adenylyl cyclase isoforms, phosphodiesterase, and protein kinase A were prepared as described by Jang et al. (2001), Cho et al. (2000), and Jang and Juhnn (2001), respectively.

Appropriate PCR conditions were chosen to ensure a linear relationship between the amount of template mRNA and the amount of amplified product mix using real-time PCR or gradient PCR. PCR products were electrophoretically separated on a 1.2% agarose gel containing ethidium bromide. The amounts of mRNA were compared using densitometric measurements of the bands obtained by Bio-Rad GS 710 Calibrated Imaging Densitometry.

DNA Synthesis

Quiescent cells were labeled with [$^3$H]thymidine (0.5 μCi/ml) for 4 hrs and the unlabeled radioactive thymidine was removed by washing with PBS. DNA was precipitated with 10% TCA and lysed in 0.5N NaOH. The radioactivity in neutralized lysates was counted in a liquid scintillation cocktail.

Measurement of Influence of Adenylyl Cyclase Inhibitor in Senescent Cell

Young or old HDF (passage 8-11) were treated with LPA (30 μM), dbcAMP (cAMP analog, 1 mM, Sigma), adenylyl cyclase inhibitor, SQ22536 (300 μM, Calbiochem) and their combinations for 30-60 min at 37° C. The cells treated were stained with Trypan blue (GiBco/BRL) for 10 min at 37° C. and only cells without blue color were then counted under hemacytometer.

In addition, the treated cells were analyzed using flow cytometry. The treated cells were harvested and treated with 1 μml of 0.1% trypsin for 30 sec, after which centrifugation was performed at 4° C. for 10 min at 1000 rpm. Then, the cell concentration was adjusted to 1-3×10$^6$ cells/ml in sample buffer. The sample buffer was prepared in such a manner that 1 g glucose in 1 L PBS without $Ca^{2+}$ and $Mg^{2+}$ was filtered through a 0.22 μm filter. The solutions containing cells was centrifuged at 4° C. for 10 min at 1000 rpm and ice-cold 70% ethanol was added dropwise to pellet. The sample tube was capped, allowed to fix in the ethanol overnight at 4° C., vortexed briefly, and then centrifuged for 5 min at 3000 rpm. Thereafter, ethanol was discarded and PI (propidium iodide) staining solution (0.5 ml 20× propidium iodide stock solution (50 μg/ml final), 1000 kunits RNase A (100 U/ml final) and 10 ml sample buffer) was added into the sample tube. Finally, the sample was analyzed within 24 hr in a slow cytometer (FACS Calibur, Beckton-Dikinson).

Results

1. Differential Changes in the Level of Intracellular $Ca^{2+}$ in Senescent Human Diploid Fibroblasts Primary human diploid fibroblasts, isolated from newborn foreskins, were used to study the mechanism of reduced response to growth factor stimulation with aging. These cells were maintained and passaged as described previously (Yeo et al., 2000a). Such senescent cells have been demonstrated to show characteristic morphological changes, enhanced beta-galactosidase activity and a reduced rate of proliferation.

Compared to their presenescent counterparts, the senescent and near-senescent cells were larger and grew to lower density, as has been observed in other cell systems. Here the present inventors report upon the differential changes in the signaling events evoked by platelet-derived growth factor (PDGF) and lysophosphatidic acid (LPA). PDGF elicits signaling events over a concentration range of 10-100 ng/ml, whereas LPA stimulates the hydrolysis of phospholipids, $Ca^{2+}$ mobilization, and actin polymerization over a concentration range of 0.1-10 μg/ml in human diploid fibroblasts. In order to compare their cellular responses, we treated presenescent and senescent (or near-senescent) cells with PDGF and LPA at a maximally responsive dose of 50 ng/ml and 1 μg/ml, respectively.

Changes in intracellular $Ca^{2+}$ were examined by confocal microscopy in presenescent and senescent fibroblasts stained with fluo-3-AM. Since senescent cells are much bigger and flatten, the number of presenescent cells was higher than that of senescent cells within the same scanned area. When the inventors repeated this experiment, they got the same results. The present inventors provided one of representative experiments in FIG. 1. PDGF and LPA showed a rapid increase in cytosolic $Ca^{2+}$ levels in presenescent fibroblasts (passage 7) and the oscillating pattern of $Ca^{2+}$ increase was agonist-specific. However, it altered in senescent cells (passage 27). The $Ca^{2+}$ response was greatly attenuated in PDGF-stimulated senescent cells (FIG. 1B) but not significantly in LPA-stimulated senescent cells (FIG. 1D).

2. Differential Changes in Actin Polymerization in Senescent Fibroblasts

Figure 2:
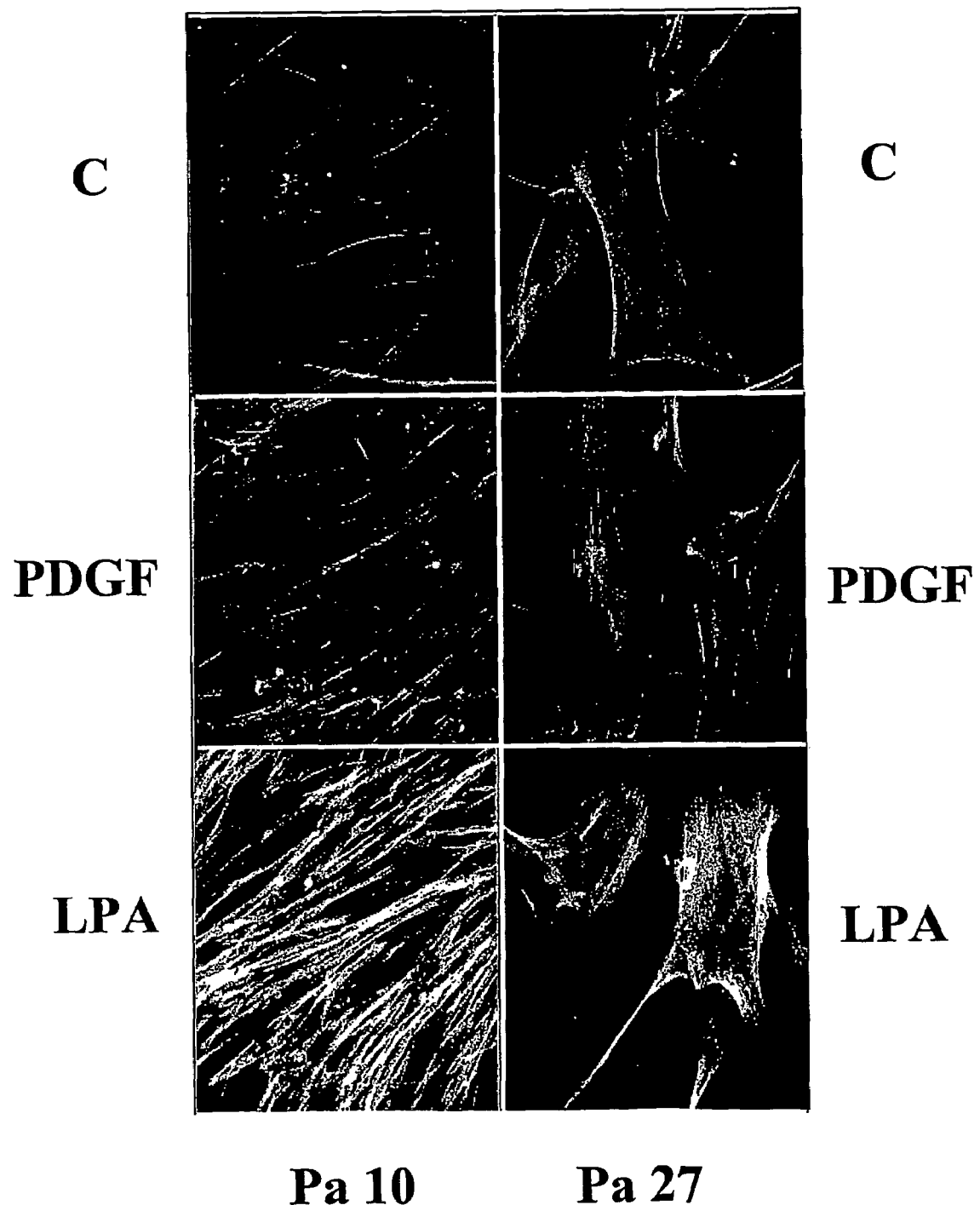
FIG. 2 represents differential changes in growth factor-induced actin polymerization in senescent fibroblasts. Presenescent (passage 10: Pa 10) and senescent fibroblasts (passage 27: Pa 27) were grown on coverslips, serum-starved, and then treated with vehicle (C), 50 ng/mll of platelet-derived growth factor (PDGF), or 1 µg/ml of lysophosphatidic acid (LPA). The cells were fixed, permeabilized, and stained with NBD-phallacidin, then photographed.

Since LPA and PDGF are $Ca^{2+}$-mobilizing agonists, actin polymerization was also examined in fibroblasts. As shown in FIG. 2, basal levels of F-actin were higher in senescent cells (passage 27) than in presenescent cells (passage 10). Both PDGF and LPA enhanced the formation of stress fibers in presenescent fibroblasts, though the changes induced by LPA were more dramatic. PDGF-induced actin polymerization was almost completely blocked, while LPA-induced actin polymerization was partially reduced in senescent cells.

Figure 3:
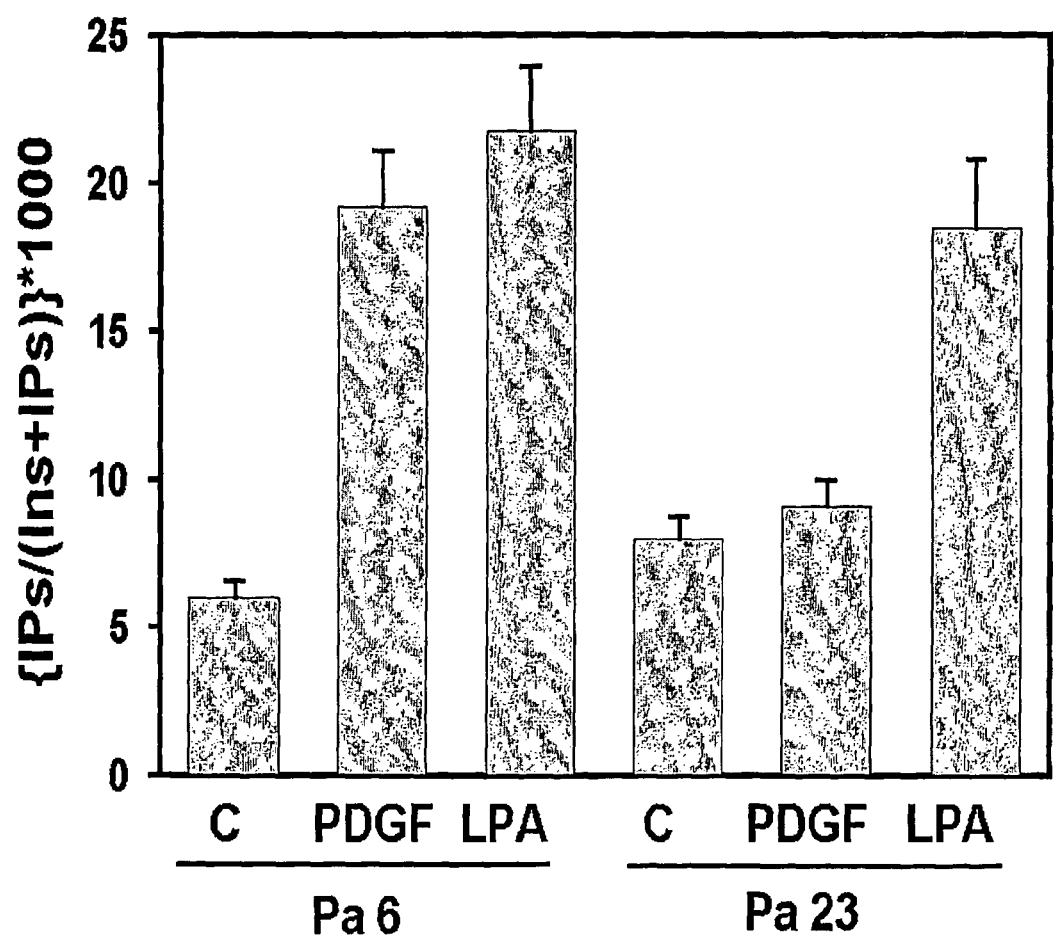
FIG. 3 shows reduction of growth factor-induced inositol phosphate production in near-senescent fibroblasts. Subconfluent presenescent (passage 6: Pa 6) and near-senescent (passage 23: Pa 23) cells were serum-starved and labeled with 0.5 µCi/ml of myo-[$^3$H]inositol overnight and then stimulated with vehicle (C), 50 ng/ml of platelet-derived growth factor (PDGF), or 1 µg/ml of lysophosphatidic acid (LPA) for 20 min in the presence of 20 mM LiCl. The accumulation of total [$^3$H]inositol phosphates was determined as described in Materials and Methods. Data are presented as the level of inositol phosphates (IPs) divided by the sum of inositol (Ins) and inositol phosphates (IPs), and are the means of a representative experiment of three, performed in triplicate.

3. Differential Changes in Agonist-Stimulated Phospholipid Hydrolysis by Phospholipase C and D in Near-Senescent Fibroblasts Phospholipase C (PLC) is activated via receptor tyrosine kinases or G-protein depending on the isoforms. One of products of PLC activation is inositol 1,4,5-trisphosphate, which induces intracellular $Ca^{2+}$ release. Since the major substrate of PLC, $PIP_2$, is also involved in the actin polymerization, the present inventors examined PLC activity by measuring the production of $IP_3$ in presenescent (passage 6) and near-senescent cells (passage 23). As shown in FIG. 3, the PDGF-stimulated inositol phosphates (IPs) production was dramatically reduced in the near-senescent cells but its level was nevertheless enhanced in LPA-stimulated senescent cells.

Figure 4:
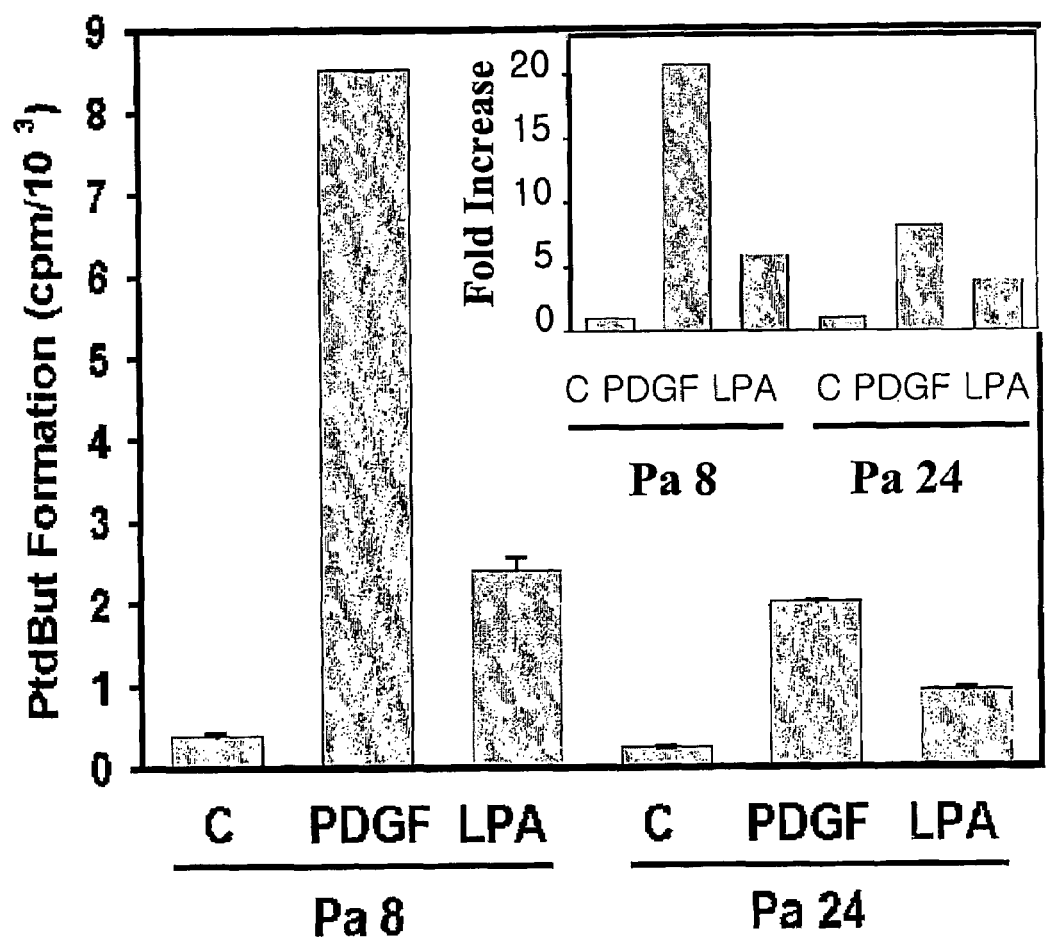
FIG. 4 demonstrates reduction of growth factor-induced phosphatidylbutanol formation in near-senescent fibroblasts. Subconfluent presenescent (passage 8: Pa 8) and near-senescent (passage 24: Pa 24) cells were serum-starved and labeled with [$^3$H]myristic acid overnight. Cells were then stimulated with vehicle (C), platelet-derived growth factor (PDGF), or lysophosphatidic acid (LPA) for 20 min in the presence of 0.5% 1-butanol. [$^3$H]phosphatidylbutanol (PtdBut) accumulation was determined as described in Materials and Methods. A representative experiment of three performed in duplicate is presented.

Since a defect in protein kinase C-dependent phospholipase D (PLD) activation has been suggested in cellular senescence and PDGF has been shown to activate PLD via protein kinase C activation, we examined the effect of aging on the activation of PLD by PDGF in fibroblasts. PLD activity was determined by measuring phosphatidylbutanol formation in the presence of 0.5% 1-butanol. As expected, the effect of PDGF and LPA on PLD activation was reduced in passage 24 near-senescent cells (FIG. 4); a reduction of PLD activity of 80% was observed in PDGF-stimulated cells. In contrast, LPA treatment showed a reduction of only ca. 20% in the near-senescent cells.

4. Differential Changes in Growth Factor-Induced DNA Synthesis in Near-Senescent Fibroblasts An age-dependent decline in DNA synthesis upon growth factor stimulation might be responsible for the rate of proliferation (Peacocke and Campisi, 1991, Smith and Pereira-Smith, 1996). By measuring [$^3$H]thymidine incorporation into DNA, the rate of DNA synthesis was determined. The basal level of [$^3$H]thymidine incorporation into DNA was greatly reduced in the passage 24 near-senescent fibroblasts. PDGF is a very strong agonist for [$^3$H]thymidine incorporation into the DNA of presenescent fibroblasts in a range of 10 to 100 ng/ml (FIG. 5A). When early passaged presenescent cells (passage 8) are quiescent with about 70% confluency, [$^3$H]thymidine incorporation was increased 7-8 fold by 50-100 ng/ml PDGF treatment. However, PDGF-induced DNA synthesis was greatly reduced in near-senescent cells, and only 1.3 fold increase in [$^3$H]thymidine incorporation was observed by 50-100 ng/ml PDGF treatment (FIG. 5B). Incubation of presenescent fibroblasts with LPA increased the level of [$^3$H]thymidine incorporation, which was apparent at 10 μg/ml and maximal at 50-70 μg/ml. Response to LPA was also reduced but less so than PDGF (FIG. 5A). When fold increase was calculated, response to 50-70 μg/ml LPA was slightly higher in the near-senescent cells (FIG. 5B). These findings correlate well with the effect on agonist-stimulated signaling events including [$Ca^{2+}$]i oscillation, in which PDGF-induced intracellular $Ca^{2+}$ release was more strongly suppressed than LPA-induced one.

5. Molecular Changes Associated with PDGF-Signaling Events

Figure 6:
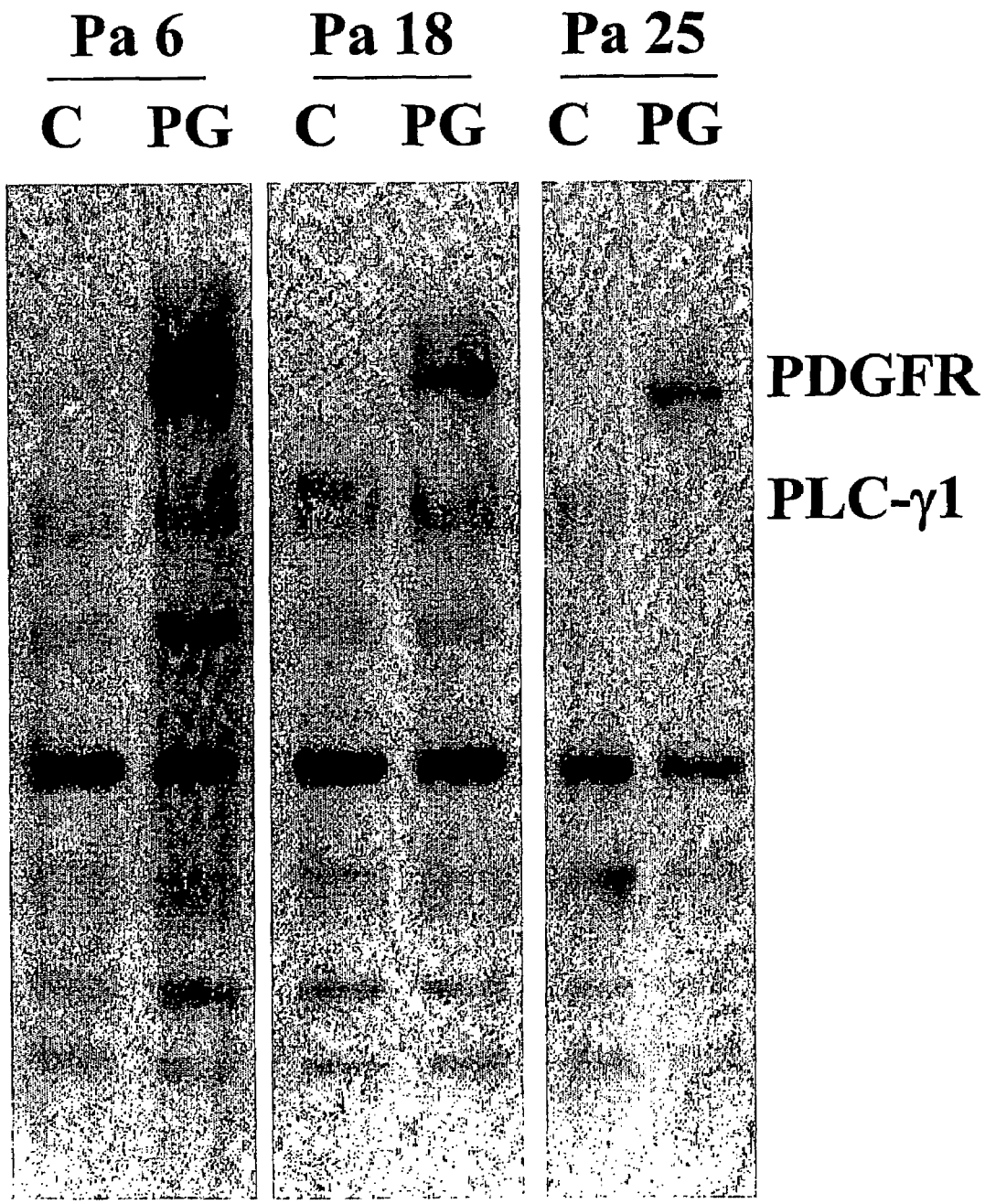
FIG. 6. represents reduction of platelet-derived growth factor-stimulated protein tyrosine phosphorylation in near-senescent fibroblasts. Subconfluent presenescent (passage 6: Pa 6), intermediate (passage 18, Pa 18), and near-senescent (passage 25: Pa 25) cells were serum-starved for 2 days and treated with vehicle (C) or 50 ng/ml of platelet-derived growth factor (PG). Cells were lysed 5 min after growth factor treatment and the tyrosine phosphorylated proteins were visualized by SDS-PAGE and Western blot analysis using polyclonal anti-phosphotyrosine antibodies. The two major tyrosine-phosphorylated bands representing platelet-derived growth factor receptor (PDGFR) and phospholipase C-γ1 (PLC-γ1) were observed.

To explore the mechanism of the reduced $Ca^{2+}$ response and $IP_3$ production upon PDGF stimulation with age, the present inventors further examined the molecular changes associated with PDGF-signaling events. PLC-γ1 is activated by binding to the autophosphorylated growth factor receptor, and subsequent tyrosine-phosphorylation by the activated receptor kinase is stimulated by the binding of the corresponding growth factor. The tyrosine phosphorylation of many proteins including PDGF receptor and PLC-γ1 was gradually reduced during cellular aging (FIG. 6). The first and second bands were both PDGF receptor itself and PLC-γ1, which was confirmed by a clearance experiment with protein A beads attaching anti-PDGF receptor and anti-PLC-γ1 antibodies (Yeo et al., 1997). Moreover, the expression level of PLC-γ1 was unchanged by increased passage, as judged by Western blot analysis (FIG. 7A). Therefore, the reduced response of senescent (or near-senescent) cells to PDGF stimulation may not be due to the altered PLC-γ1 protein. To test whether the dramatic decreases in the PDGF-induced signaling events are due to a reduction of the PDGF receptor itself, we further examined the level of PDGF receptors using polyclonal anti-human PDGF type A/B receptor antibodies. Although the antibodies recognize both PDGF type A (170 kDa) and B (190 kDa) receptors, fibroblasts contain predominantly the B-type receptor. The expression of PDGF receptor type B was found to be gradually downregulated during cellular aging (FIG. 7B).

Since PLD activity was reduced in the PDGF-stimulated near-senescent cells, some proteins involved in PLD activation, other than PDGF receptor, such as PKC and PLD isoforms might also have been modulated with age. No change in the level of PKCs was detected as determined by Western blot analysis (FIG. 8A), but a gradual decrease in the level of PLD1 protein was observed during the aging process (FIG. 8B).

6. LPA-Induced cAMP Signaling is Altered in Near-Senescent Human Diploid Fibroblasts To study the differential changes of growth factor-stimulated signal transduction system in senescent cells, we investigated the aging effect on cAMP signaling in response to a physiological lipid mitogen lysophosphatidic acid (LPA). Under basal conditions cellular cAMP was 37.0+/−2.6 and 36+/−3.1 pmol/ml protein in presenescent (Passage 8) and near-senescent (Passage 27) fibroblasts, respectively. In presenescent fibroblasts, cellular cAMP decreased by 33-43% after a 30 min incubation with LPA over a concentration range of 1-70 µg/ml (FIG. 9A). In contrast, LPA incubation increased cellular cAMP by 31-77% in near-senescent fibroblasts. A dose of 30 µg/ml LPA efficiently induced a decrease in cAMP in presenescent cells (FIG. 9A). Time-dependent profile of cAMP response was also altered in near-senescent LPA-stimulated cells. LPA Incubation of near-senescent fibroblasts with 30 µg/ml LPA for 60 min increased cellular cAMP content by 70-80% (FIG. 9B).

7. Changes in Protein Kinase A Activity and CREB Phosphorylation by LPA Treatment PKA is activated in response to CAMP accumulation. As expected, PKA activity is correlated well with the altered profile of cAMP content. PKA activity was decreased by LPA treatment in presenescent cells but it was increased in near-senescent cells (FIG. 10A). CREB phosphorylation is one of cAMP-induced responses for the regulation of gene expression. CREB phosphorylation was correlated well with cAMP accumulation and subsequent PKA activation occurred in LPA-stimulated near-senescent fibroblasts (FIG. 10B).

8. Changes in Adenylyl Cyclase and Phosphodiesterase Activities Occurred in Senescent Cells cAMP is generated by activated adenylyl cyclases (ACs) and degraded by activated phosphodiesterases (PDEs). The ability to breach the PKA activation threshold can depend upon either or both the activation of AC and inhibition of specific PDE isoforms. To test whether the activity or protein contents of either ACs or PDEs are altered by aging, the inventors first examined total AC and PDE activities. As shown in FIG. 11A, total AC activity was reduced time-dependently by LPA in presenescent cells, but increased in the near-senescent cells. In contrast, upon LPA simulation, PDE activity was increased in presenescent cells and reduced in near-senescent cells (FIG. 10B).

9. Differential Changes in LPA Receptors

To explore the mechanism of enhanced cAMP accumulation by LPA in senescent human diploid fibroblasts, the present inventors further examined changes in LPA receptors and G-proteins involved in cAMP-signaling events. In addition to the major members of the EDG family interacting with LPA, EDG-2, EDG-4 and EDG-7, a low affinity LPA receptor EDG1 was also examined. Specific mRNA transcripts for the human LPA-receptors were detected by semi-quantitative RT-PCR with specific primers and the densitometric analysis of each product. The inventors detected mRNA transcripts for EDG-1, EDG-2, EDG-4, and EDG-7 (EDG1>EDG2>EDG4>EDG7) in presenescent human diploid fibroblasts (FIG. 12). The inventors found that the levels of EDG-1 and -4 mRNA were unaltered by age, whereas the levels of EDG-2 and -7 decreased slightly in the near-senescent fibroblasts.

10. Differential Changes in G Proteins.

The cAMP system is one of important G-protein signaling systems. Some extracellular signals bind to and activate their seven transmembrane receptors, which couple to stimulatory G proteins (Gsα) or inhibitory G proteins (Giα) to regulate adenylyl cyclase (AC). The LPA receptor EDG-2 is coupled to pertussis toxin-sensitive Gi, whereas EDG4 is coupled to both Gi and Gq (An et al., 1998), and EDG7 to a pertussis toxin-insensitive G-protein(s), possibly Gq (Bandoh et al., 1999; Im et al., 2000). Among the subunits of G proteins involved in the regulation of adenylyl cyclases, Giα directly inhibit some of AC isoforms and Gq indirectly stimulates or inhibits some of AC isoforms indirectly via $Ca^{++}$ and/or calmodulin. Therefore, the mRNA level of G proteins was also examined by semi-quantitative RT-PCR. As shown in FIG. 13, the mRNA level of Gq was unaltered during the aging process. Moreover, the mRNA levels of Gi1, Gi2, and Gi3 decreased in the near-senescent cells.

11. Changes in the Expression of Adenylyl Cyclase, Phosphodiesterase and Protein Kinase A Isoforms Occurred in Senescent Cells Since the isoform multiplicity of AC, PDE, and PKA plays an important role in the regulation of cAMP signaling (Houslay and Milligan, 1997), the present inventors further examined the isoform expression of these enzymes at the transcription level by semi-quantitative RT-PCR with specific primers. Each RT-PCR product was electrophoretically seperated on an agarose gel containing ethidium bromide and photographed for the densitometric analysis. The results of semi-quantitative RT-PCR were confirmed by real-time PCR.

At least nine genes for mammalian AC have been cloned (Sunahara et al., 1996). AC isoforms possess a wealth of common and disparate features. All isoforms are activated by both forskolin and the GTP-bound Gsα, and they are inhibited by certain adenosine analogs such as 2'-deoxy-3'-AMP. All of the AC isoforms are further regulated in type-specific patterns by other signaling inputs, including calcium ions, other G protein subunits (Gi/oα, Gqα and βγ), and protein kinase C (Taussig and Gilman, 1995; Sunahara et al., 1996). In presenescent human diploid fibroblasts, ACII, ACIV, ACVI, and ACIX mRNAs were detected by this experimental method. The expression of ACII, ACIV, and ACVI was increased, while that of ACIX was decreased in the near-senescent fibroblasts (FIG. 14A).

Cellular cAMP can be hydrolyzed and inactivated by the cyclic nucleotide phosphodiesterase (PDE). Mammalian PDEs are encoded by at least 19 different genes. The use of different transcriptional units and exon splicing of a single PDE gene generates proteins with different regulatory domains joined to a common catalytic domain, therefore expanding the array of isoforms with subtle differences in properties and sensitivities to different signals (Conti and Jin, 1999). Among 19 PDE genes, type 4B and 4C were expressed mainly in presenescent human diploid fibroblasts (FIG. 14B). The mRNA levels of type 1A/B, 1C, and 3A were increased in the near-senescent states. The mRNA level of 4B was slightly decreased but that of 4C was unaltered in the near-senescent states.

The mRNA expression of PKA catalytic subunits and regulatory subunits was also compared between presenescent and near-senescent fibroblasts (FIG. 6). The PKA catalytic subunit Cα, regulatory subunit RIα and RIβ were increased but regulatory subunit RIIα was decreased with age.

12. Changes in PKC and ERK Activation by LPA

ACII is a PKC-stimulated isoform. An increase in ACII might confer the PKC-dependency in AC activation by LPA in the near-senscent fibroblasts. The present inventors examined the cAMP content in LPA-stimulated near-senescent HDF in the presence of PKC inhibitor bis-indolylmaleiamide. As expected, the inventors observed an inhibition of cAMP accumulation in the presence of Protein kinase C inhibitor (FIG. 15).

Since LPA stimulates phospholipase C via Gq and produces a calcium oscillation, calcium-dependent PKC could be activated. Since both calcium and PKC are regulators of AC activities, the inventors further confirmed that LPA controls the PKC activity in both presenescent and near-senescent HDF (FIG. 16). Basal level of PKC activation was higher in near-senescent HDF than in presenescent HDF. Although the magnitude of increase in PKC activation was lower, there was a further increase in PKC activation by LPA in near-senescent cells.

ERK can be stimulated by LPA presumably via the βγ subunits of Gi or via the activated PKC/PLD pathway. Since Raf, an upstream regulator of ERK, is inhibited by cAMP-dependent protein kinase A, the inventors further examined the ERK activity induced by LPA. The level of ERK activation was examined by comparing the level of phospho-ERK by Western blot analysis. As shown in FIG. 17, both ERK1 and ERK2 were stimulated by LPA treatment for 10-30 min and returned to the basal level after 60 min treatment in presenescent HDF. The basal level of ERK phosphorylation was enhanced but LPA did not increase further the level of phospho-ERK.

13. Changes in DNA Synthesis and Cell Proliferation Induced by LPA

An age-dependent decline in DNA synthesis upon LPA stimulation was examined by measuring [$^3$H]thymidine incorporation into DNA. The basal level of [$^3$H]thymidine incorporation into DNA was greatly reduced in the near-senescent fibroblasts. Incubation of presenescent fibroblasts with LPA increased the level of [$^3$H]thymidine incorporation, which was apparent at 10 μg/ml and maximal at 50-70 μg/ml. Response to LPA was also reduced in the near-senescent cells (FIG. 18A). When fold increase was calculated, response to 50-70 μg/ml LPA was slightly higher in the senescent cells (FIG. 18B).

In order to study the role of LPA-induced cAMP signaling, the inventors further compared LPA-stimulated cell proliferation between presenescent and near-senescent cells. After 4 days treatment with vehicle or LPA, the level of viable cells were counted or measured by MTT assay. LPA stimulated proliferation of presenescent cells dose-dependently but the rate of proliferation partially decreased in near-senescent cells (FIG. 19).

14. Recovery in DNA Synthesis and Cell Proliferation in Senescent Cell by Adenylyl Cyclase Inhibitor Recovery in DNA synthesis and cell proliferation in senescent cell by treatment of adenylyl cyclase inhibitor was investigated by flow cytometry and cell counting. The viable cell number in senescent cell culture was dramatically increased by virtue of treating LPA plus adenylyl cyclase inhibitor, of which pattern was shown to be closely similar to young cell. In other words, the cell proliferation in senescent cell was changed to an increasing pattern (FIG. 20).

As shown in FIG. 21, flow cytometry analysis reveals that the number of cells in S phase was dramatically increased in senescent cell by treatment of adenylyl cyclase inhibitor. Such increase was more enhanced by co-treatment of adenylyl cyclase inhibitor with LPA.

Consequently, it is understood that the senescent cell can be changed to young cell with treatment of adenylyl cyclase inhibitor in terms of various physiological phenotypes and a response to LPA in senescent cell can be restored by treatment of adenylyl cyclase.

Having described a preferred embodiment of the present invention, it is to be understood that variants and modifications thereof falling within the spirit of the invention may become apparent to those skilled in this art, and the scope of this invention is to be determined by appended claims and their equivalents.

REFERENCES

1. Alvarez, E., Ruiz-Gutierrez, V., Santa Maria, C., Machado, A., 1993. *Mech. Aging Dev.* 71, 1-12.
2. An, S., Bleu, T., Hallmark, O. G., and Goetzl, E. J. (1998a) *J. Biol. Chem.*, 273, 7906-7910.
3. An, S., Bleu, T., Zheng, Y., and Goetzl, E. J. (1998b) *Mol. Pharmacol.* 54, 881-888.
4. An, S., Goetzl, E. J., Lee, H., 1998c. *J. Cell. Biochem. Suppl.* 30-31:147-157.
5. Aoyagi, M., Fukai, N., Ogami, K., Yamamoto, M., Yamamoto, K., 1995. *J. Cell Physiol.* 164, 376-84.
6. Bandoh, K., Aoki, J., Hosono, H., Kobayashi, S., Kobayashi, T., Murakami-Murofushi, K., Tsujimoto, M., Arai, H., and Inoue, K. 1999. *J. Biol. Chem.*, 274, 27776-27785.
7. Blalock, E. M., Porter, N. M., Landfield, P. W., 1999. *J. Neurosci.* 19, 8674-8684.
8. Blumenthal, E. J., Miller, A. C., Stein, G. H., Malkinson, A. M., 1993. *Mech. Ageing Dev.* 72, 13-24.
9. Boyce, S. T., Ham, R. G., 1983. *J. Invest. Dermatol.* 81, 33S-40S.
10. Chin, J. H., Hoffman, B. B., 1991. *Mech. Ageing Dev.* 57, 259-273.
11. Chin, J. H., Okazaki, M., Frazier, J. S., Hu, Z. W., Hoffman, B. B., 1996. *Am. J. Physiol.* 271, C362-371.
12. Cho, C. H., Cho, D. H., Seo, M. R., Juhnn, Y. S., 2000. *Exp. Mol. Med.* 32, 110-114.
13. Chomczynski, P., and Sacchi, N. (1987) *Anal. Biochem.* 162, 156-159.
14. Cohen, B. M., Zubenko, G. S., 1985. *Life Sci.* 37, 1403-1409.
15. Conti, M., Jin, S. L., 1999. *Prog. Nucleic Acid Res. Mol. Biol.* 63, 1-38.
16. Contos, J. J., Ishii, I., Chun, J., 2000. *Mol. Pharmacol.* 58, 1188-1196.
17. Dimri, G. P., Campisi, J., 1994. *Exp. Cell. Res.* 212, 132-140.
18. Eckert, A., Hartmann, H., Forstl, H., Muller, W. E., 1994. *Life Sci.* 55, 2019-2029.
19. Ethier, M. F., Medeiros, M., Romano, F. D., Dobson, J. G. Jr., 1992. *Exp. Gerontol.* 27, 287-300.
20. Figler, R. A., Graber, S. G., Lindorfer, M. A., Yasuda, H., Linden, J., and Garrison, J. C. (1996) *Mol. Pharmacol.* 50, 1587-1595.
21. Fukushima, N., Ishii, I., Contos, J. J., Weiner, J. A., Chun, J., 2001. *Annu. Rev. Pharmacol. Toxicol.* 41, 507-534.
22. Gerhard, G. S., Phillips, P. D., Cristofalo, V. J., 1991. *Exp. Cell. Res.* 193, 87-92.
23. Gohla, A., Harhammer, R., Schultz, G., 1998. *J. Biol. Chem.* 273, 4653-4659.
24. Ha, K. S., Exton, J. H., 1993. *J. Cell. Biol.* 123, 1789-1796.
25. Ha, K. S., Yeo, E. J., and Exton, J. H. (1994) *Biochem. J.* 303, 55-59.
26. Hecht, J. H., Weiner, J. A., Post, S. R., and Chun, J. (1996) *J. Cell Biol.* 135, 1071-1083.
27. Hensler, P. J., Pereira-Smith, O. M., 1995. *Am. J. Pathol.* 147, 1-8.
28. Houslay, M. D., Milligan, G., 1997. *Trends Biochem. Sci.* 22, 217-224.

29. Huang, H. M., Toral-Barza, L., Thaler, H., Tofel-Grehl, B., Gibson, G. E., 1991. *Neurobiol Aging* 12, 469-473.
30. Huang, M. S., et al., 2000. *Am. J. Physiol. Renal. Physiol.* 278, F576-84.
31. Huang, M. S., et al., 1998. *Biochem. Biophys. Res. Comm.* 245, 50-52.
32. Igwe, O. J., Ning, L., 1993. *Neurosci. Lett.* 164, 167-170.
33. Ishii. I, Contos, J. J., Fukushima, N., Chun, J., 2000. *Mol. Pharmacol.* 58, 895-902.
34. Ishikawa, Y., Gee, M. V., Ambudkar, I. S., Bodner, L., Baum, B. J., Roth, G. S., 1988. *Biochim. Biophys. Acta* 968, 203-210.
35. Jalink, K., van Corven, E. J., and Moolenaar, W. H. (1990) *J. Biol. Chem.* 265, 12232-12239.
36. Jang, I. S., Juhnn, Y. S., 2001. *Exp. Mol. Med.* 33, 37-45.
37. Jang, I. S., Kang, U. G., Kim, Y. S., Ahn, Y. M., Park, J. B., Juhnn, Y. S., 2001. *Prog. Neuropsychopharmacol. Biol. Psychiatry,* 25, 571-581
38. Junn, E., et al., 2000. *J. Immunol.* 165, 2190-2197.
39. Lee, M.-J., Thangada, S., Liu, C. H., Thompson, B. D., and Hla, T. (1998) *J. Biol. Chem.* 273, 22105-22112.
40. Lin, W. W., Chang, S. H., Wang, S. M., 1999. *Br. J. Pharmacol.* 128, 1189-1198.
41. Lipschitz, D. A., Udupa, K. B., Indelicato, S. R., Das, M., 1991. *Blood* 78, 1347-1354.
42. Liu, A. Y., Chang, Z. F., Chen, K. Y., 1986. *J. Cell. Physiol.* 128, 149-154.
43. Liu, P., Wang, P. Y., Michaely, P., Zhu, M., Anderson, R. G. W., 2000. *J. Biol. Chem.* 275, 31648-31654.
44. Liu, P., Ying, Y., Ko, Y. G., Anderson, R. G. W., 1996. *J. Biol. Chem.* 271, 10299-10303.
45. Matsuda, T., Okamura, K., Sato, Y., Morimoto, A., Ono, M., Kohno, K., Kuwano, M., 1992. *J. Cell. Physiol.* 150, 510-516.
46. Matsuoka, I., Suzuki, Y., Defer, N., Nakanishi, H., Hanoune, J., 1997. *J. Neurochem.* 68, 498-506.
47. Meacci, E., Vasta, V., Faraoni, P., Farnararo, M., Bruni, P., 1995. *Biochem. J.* 312, 799-803.
48. Moolenaar, W. H., Kranenburg, O., Postma, F. R. and Zondag, G. C. M. (1997) *Curr. Opinion. Cell Biol.* 9, 168-173.
49. Mori, S., Kawano, M., Kanzaki, T., Morisaki, N., Saito, Y., Yoshida, S., 1993. Eur. J. Clin. Invest. 23, 161-165.
50. Nicoletti, A., and Sassy-Prigent, C. (1996) *Method. Anal. Biochem.* 236, 229-241.
51. Park, J. S., Park, W. Y., Cho, K. A., Kim, D. I., Jhun, B. H., Kim, S. R., Park, S. C., 2001. *FASEB J.* 15, 1625-1627.
52. Park, W. Y., Park, J. S., Cho, K. A., Kim, D. I., Ko, Y. G., Seo, J. S., Park, S. C., 2000. *J. Biol. Chem.* 275, 20847-20852.
53. Pascale, A., Govoni, S., Battaini, F., 1998. *Mol. Neurobiol.* 16, 49-62.
54. Paulsson, Y., et al., 1986. *EMBO J.* 5, 2157-2162.
55. Peacocke, M., Campisi, J., 1991. *J. Cell. Biochem.* 45, 147-155.
56. Peterson, C. Goldman, J. E., 1986. *Proc. Natl. Acad. Sci. USA* 83, 2758-2762.
57. Peterson, C., Ratan, R. R., Shelanski, M. L., and Goldman, J. E. (1988) *Neurobiol Aging* 9, 261-266.
58. Peterson, C., Ratan, R. R., Shelanski, M. L., and Goldman, J. E., 1986. *Proc. Natl. Acad. Sci. USA* 83, 7999-8001.
59. Psarras, S., Kletsas, D., and Stathakos, D. (1994) *FEBS Lett.* 339, 84-88.
60. Ribault, D., Habib, M., Abdel-Majid, K., Barbara, A., Mitrovic, D., 1998. *Mech. Ageing Dev.* 100, 25-40.
61. Ridley, A. J., Hall, A., 1992. *Cell* 70, 389-399.
62. Robert, A., Tran, N. N., Giummelly, P., Atkinson, J., Capdeville-Atknson, C., 1998. *Am. J. Physiol.* 274, R1604-1612.
63. Shah, B. H. (1999) *Exp. & Mol. Med.* 31, 89-94.
64. Shin, E. A., et al., 1999. *FEBS Lett.* 452, 355-359.
65. Shiraha, H., Gupta, K., Drabik, K., Wells, A., 2000. *J. Biol. Chem.* 275, 19343-19351.
66. Smith, J. R., Pereira-Smith, O. M., 1996. *Science* 273, 63-67.
67. Sunahara, R. K., Dessauer, C. W., Gilman, A. G., 1996. *Annu. Rev. Pharmacol. Toxicol.* 36, 461-480.
68. Takano, K., Yasufuku-Takano, J., Teramoto, A., and Fujita, T. (1997) *Endocrinology* 138, 2405-2409.
69. Taussig, R., Gilman, A. G., 1995. *J. Biol. Chem.* 270, 1-4.
70. Taussig, R., Iniguez-Lluhi, J. A., Gilman, A. G., 1993. *Science* 261, 218-221.
71. Venable, M. E., Blobe, G. C., Obeid, L. M., 1994. *J. Biol. Chem.* 269, 26040-26044.
72. Venable, M. E., Obeid, L. M., 1999. *Biochim. Biophys. Acta* 1439, 291-298.
73. Wang, J., Walsh, K., 1996. *Science* 273, 359-361.
74. Wen, Y. Y., Wang, S. X., Chen, M. Q., 1999. *Clin. Exp. Pharmacol. Physiol.* 26, 840-841.
75. Xu, J., et al., 2000. *J. Biol. Chem.* 275, 27520-27530.
76. Yamamoto, M., Toya, Y., Jensen, R. A., Ishikawa, Y., 1999. *Exp. Cell Res.* 247, 380-388.
77. Yang, J. M., Cho, C. H., Kong, K. A., Jang, I. S., Kim, H. W., Juhnn, Y. S., 1999. *Exp. Mol. Med.* 31, 179-184
78. Yeo, E. J., et al., 2000b. Exp. Gerontol. 35, 553-571.
79. Yeo, E. J., Hwang, Y.-C., Kang, C. M., Choy, H. E., Park. S. C., 2000a. *Mol Cells* 10, 415-422.
80. Yeo, E. J., Kazlauskas, A., Exton, J. H., 1994. *J. Biol. Chem.* 269, 27823-27826.
81. Yeo, E. J., Proost, J. J., Exton, J. H., 1997. *Biochim. Biophys. Acta.* 1356, 308-320.

What is claimed is:

1. A method for inhibiting cellular senescence in a human fibroblast cell, said method comprising treatment to the cell in the amount from 1 to 500 μM of an inhibitor of adenylyl cyclase to inhibit said cyclase.

2. The method according to claim 1, wherein the adenylyl cyclase is adenylyl cyclase II, adenylyl cyclase IV or adenylyl cyclase VI.

3. The method according to claim 1, wherein said inhibiting of cellular senescence is restored and changed a senescent cell to a young cell.

4. The method according to claim 1, wherein the inhibitor of adenylyl cyclase is selected from 2',5'-dideoxyadenosine, cis-N-(2phenyylcyclopentyl)azacyclotridec-1-en-2-amine and 9-(tetrahydro-2'-furyl)adenine.

* * * * *